US006810300B1

(12) United States Patent
Woltman et al.

(10) Patent No.: US 6,810,300 B1
(45) Date of Patent: Oct. 26, 2004

(54) METHOD OF DESIGNING A PRODUCT WORN ON A BODY IN A VIRTUAL ENVIRONMENT

(75) Inventors: Garry Roland Woltman, Greenville, WI (US); Sara Jane Wille Stabelfeldt, Appleton, WI (US); Yung Hsiang Huang, Appleton, WI (US); Deanna R. Kathumbi-Jackson, Atlanta, GA (US); John E. Kerins, Neenah, WI (US); Jan E. Carr, Denver, CO (US); Christopher M. Pieper, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/447,919

(22) Filed: May 22, 2003

(51) Int. Cl.[7] ............................................... G06F 19/00
(52) U.S. Cl. ......................... 700/132; 700/303; 702/167
(58) Field of Search ................................. 700/132, 131, 700/130, 303; 702/155, 166, 167; 703/2

(56) References Cited

U.S. PATENT DOCUMENTS

| | | | |
|---|---|---|---|
| 4,539,585 A | 9/1985 | Spackova et al. | |
| 4,546,434 A | 10/1985 | Gioello | |
| 4,598,376 A | 7/1986 | Burton et al. | |

(List continued on next page.)

FOREIGN PATENT DOCUMENTS

| | | | |
|---|---|---|---|
| EP | 0 205 683 A1 | 12/1986 | |
| EP | 0 887 055 A1 | 12/1998 | |
| EP | 1 124 191 A2 | 8/2001 | |
| WO | WO 97/45088 A1 | 12/1997 | |
| WO | WO 99/18487 A2 | 4/1999 | |
| WO | WO 00/38117 A1 | 6/2000 | |
| WO | WO 01/20517 A2 | 3/2001 | |

(List continued on next page.)

OTHER PUBLICATIONS

Zhang et al., "Numerical Simulation of 3D Dynamic Garment Pressure", Textile Research Journal, Mar. 2002, vol. 72, No. 3, pp. 245–252, TRI/Princeton, New Jersey, www.textileresearchjournal.com.

Doyle, "Virtual Engineering: Toward a Theory for Modeling and Simulation of Complex Systems", vol. 9: Modeling and Simulation, Appendix B, Aug. 9, 2001, www.nap.edu/html/tech 21st/msb.htm.

*Primary Examiner*—Peter Nerbun
(74) *Attorney, Agent, or Firm*—Senniger Powers

(57) ABSTRACT

A method of designing a product for use on a body used to develop a preferred product configuration using a computer-based virtual product development and testing system. A virtual wearer sub-model is created of the body and a virtual product sub-model is created of a product for use on the body. An environment sub-model is generated so that environmental factors affecting the product or the body are also used in designing or evaluating the product. Instructions defining how the wearer sub-model, the product sub-model and the environment sub-model interact are introduced in an interaction model. The sub-models and the interaction defined by the interaction model are then combined to create a virtual use model simulating the use of the virtual product sub-model by the virtual wearer sub-model. The use model determines the forces, deformations and stresses caused by movement and interaction between the virtual wearer sub-model and the virtual product sub-model using numerical method analysis. The results of the use model are analyzed to evaluate the performance of product features embodied in the virtual product sub-model such as when positioned on a virtual wearer and exposed to typical movements or forces. The analysis evaluates the performance of at least one product feature of the product and/or wearer body. The product sub-model is then modified in response to the determined performance of the product feature and the steps of interacting the models and combining the models are reperformed in the use model to design the product.

37 Claims, 22 Drawing Sheets

U.S. PATENT DOCUMENTS

| | | |
|---|---|---|
| 4,885,844 A | 12/1989 | Chun |
| 5,163,006 A | 11/1992 | Deziel |
| 5,163,007 A | 11/1992 | Slilaty |
| 5,208,765 A | 5/1993 | Turnbull |
| 5,341,305 A | 8/1994 | Clarino et al. |
| 5,495,568 A | 2/1996 | Beavin |
| 5,548,519 A | 8/1996 | Park et al. |
| 5,680,528 A | 10/1997 | Korszun |
| 5,682,506 A | 10/1997 | Corby, Jr. et al. |
| 5,724,522 A | 3/1998 | Kagami et al. |
| 5,768,135 A | 6/1998 | Park et al. |
| 5,850,222 A | 12/1998 | Cone |
| 5,864,480 A | 1/1999 | Ladd |
| 5,956,525 A | 9/1999 | Minsky |
| 6,070,269 A | 6/2000 | Tardif et al. |
| 6,093,027 A | 7/2000 | Unger et al. |
| 6,101,424 A | 8/2000 | Sawada |
| 6,256,038 B1 | 7/2001 | Krishnamurthy |
| 6,307,568 B1 | 10/2001 | Rom |
| 6,324,437 B1 | 11/2001 | Frankel et al. |
| 6,488,202 B1 | 12/2002 | Seitz et al. |
| 6,701,207 B1 * | 3/2004 | Gazzuolo .................... 700/132 |
| 6,711,455 B1 * | 3/2004 | Holloway et al. .......... 700/132 |
| 6,725,124 B2 * | 4/2004 | Yan ........................... 700/132 |

FOREIGN PATENT DOCUMENTS

| | | |
|---|---|---|
| WO | WO 01/39584 A2 | 6/2001 |
| WO | WO 01/46911 A1 | 6/2001 |
| WO | WO 01/52140 A1 | 7/2001 |
| WO | WO 01/53910 A2 | 7/2001 |
| WO | WO 01/75771 A1 | 10/2001 |

\* cited by examiner

FIG. 4
FIG. 5
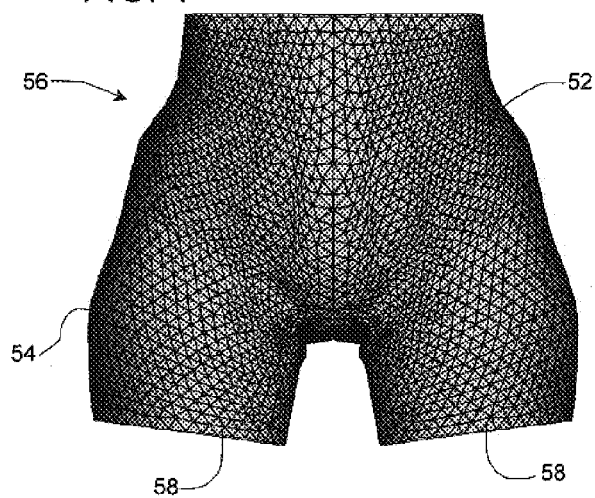
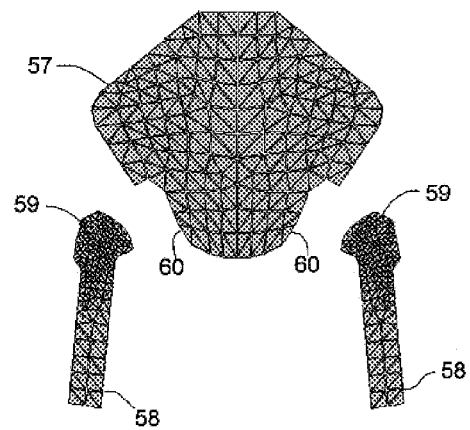

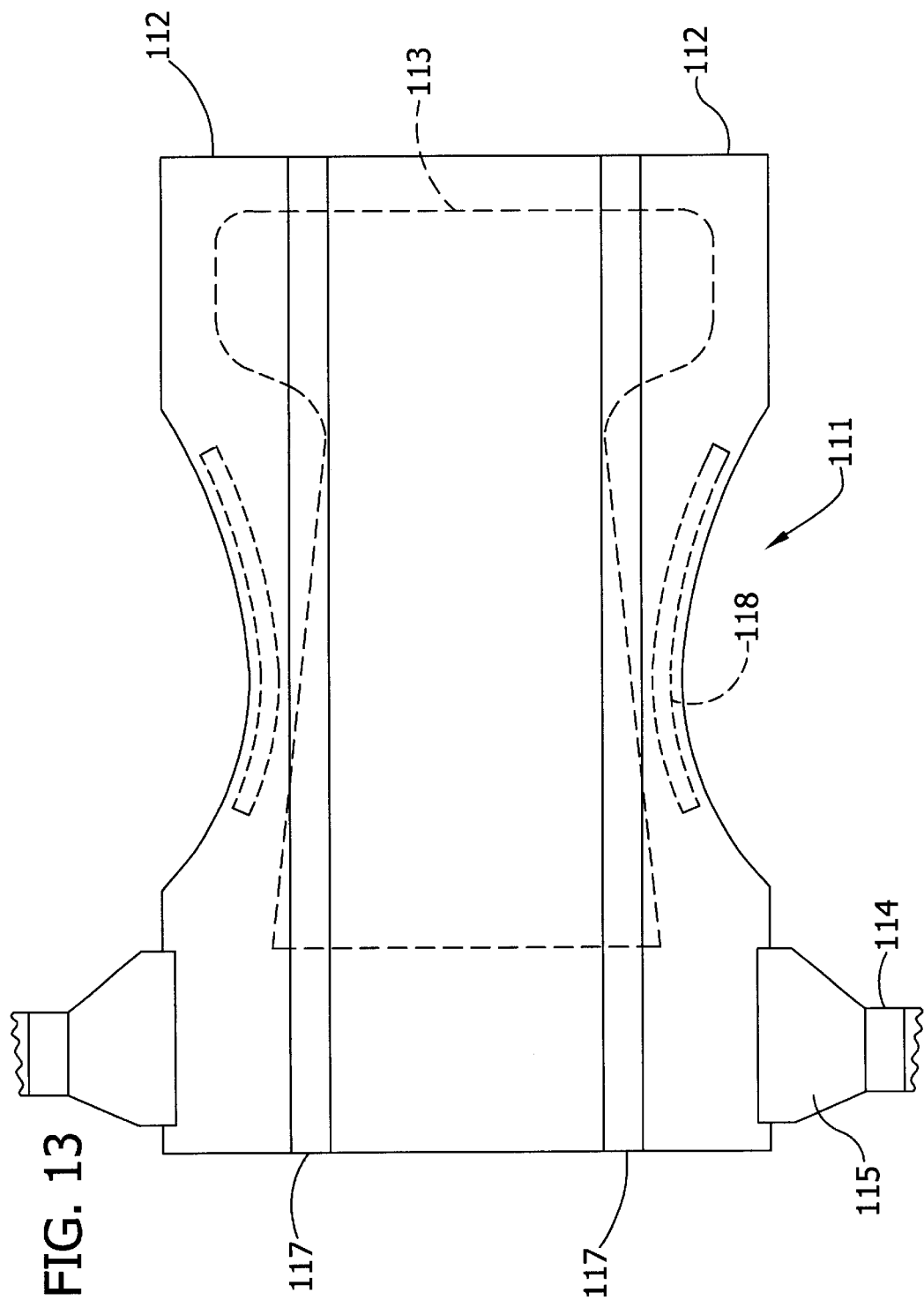

METHOD OF DESIGNING A PRODUCT WORN ON A BODY IN A VIRTUAL ENVIRONMENT

BACKGROUND OF THE INVENTION

This invention relates generally to evaluation of articles positioned on a body, and in particular to a computer-based simulation system for designing and evaluating articles with a comfortable fit to a human body across a body's range of motion.

Clothing and other articles which are used on the body should interface with the body so as to be comfortable when the user is stationary, such as when standing or sitting, and also during movement, such as when walking. One ideal article would fit against the user's body with suitable contact pressure sufficient to hold the article in place but without constricting the skin or degrading comfort. This is challenging because of the wide variation in body shapes of potential users and the various potential material properties the article may have can affect the interactions between the body and the article.

Body fit is often influenced by size or shape of the article but is also characterized by less tangible descriptions such as moving with the body or being less noticeable while wearing. Fit depends on an initial position of the article relative to the body and any subsequent user movements which shift relative positions, deflect the article's shape, and/or cause the article to apply greater or lesser pressure against the user's body. Comfort is influenced by multiple factors including the shape of the user's body, mechanical properties of the underlying bodily tissue, the shape and size of the article, mechanical properties of the article, and interactions between the article and any other adjacent articles. These properties are highly three-dimensional in nature and are not easily analyzed when designing a new article or improving an existing article's configuration.

In addition to comfort, articles may have functional requirements which aggravate the difficulty in finding a satisfactory article configuration. For example, absorbent products for personal care and/or personal protective use, such as disposable diapers, disposable pants, medical garments, feminine hygiene products, incontinence products, medical drapes, facemasks and barrier products, should fit well against the body not only for comfort, but also for effectiveness in absorbing bodily exudates without leakage. A product of this type that fails to fit well may apply undesired pressure against the user's body or contain gaps or openings that can cause the product to fail functionally. For example, as a person stands up from a seated position or walks, his or her thighs may squeeze a diaper or other absorbent product and may deform it in a manner that results in leakage of fluid.

The development of new or improved products that avoid these problems is complex due to the large number of potential shapes, contours, sizes, component materials, and material distributions. The advent of newer materials with an improved range of compressive and elastic properties and less bulk emphasizes a need to understand the complex interactions between the body and the product. Unfortunately, the process of identifying an acceptable or optimum combination of design parameters which is functionally effective and comfortable across a normal range of user body shapes and motions is time consuming and becomes a substantial expense.

New products are typically defined with initial reliance on historical data, and are subsequently tested both in physical laboratories and in wearer use. Such tests use sample products in conjunction with human test subjects or physical models of test subjects. Unfortunately, physical testing has many limitations. The sample products can be constructed only with readily available materials and construction techniques. Even if materials and construction techniques are available, the time and expense of assembling a variety of sample articles for testing can be substantial and potentially prohibitive. Testing procedures are limited to available and acceptable physical tests. These tests, when available, are limited by their physical nature including safety issues, which are especially applicable as they relate to human-use testing. Moreover, the resources needed for human-use testing can be enormous and the time required for that testing could delay market entry. One can go through considerable time and expense to find out that a material or product idea will not work.

SUMMARY OF THE INVENTION

Among the several objects and features of the present invention may be noted the provision of method to simulate movement of a product positioned on a moving body; a method to simulate the wearing of a product on the human body; the provision of such a method which assesses body fit, comfort, or functional performance of the article; and the provision of such a method which provides a three-dimensional dynamic simulation of deformation of the article and human body across a user's range of motion.

Additionally, the invention may include the provision of such a method of screening a number of variant design features on the article; the provision of such a method which characterizes and controls the relationship between a body, a product and an environment with respect to fit and comfort; and the provision of such a method which facilitates development of a product free from physical testing in a virtual, computer-based system.

In one embodiment, the invention is a method of designing a product to be worn on a body. The method includes creating a computer based body sub-model of at least a portion of the body on which the product is to be positioned and creating a computer based product sub-model of the product. The method also includes defining an environment in which the body sub-model interacts with the product sub-model with an environment sub-model. The method further includes interacting the body sub-model, the product sub-model, and the environment sub-model with movement of one or more of the sub-models with an interaction model. Next, the body sub-model, the product sub-model, the environment sub-model and the interaction model are combined in a use model simulating the interaction between the body sub-model, the product sub-model and the environment sub-model to produce a representation of at least one product feature of the product. The method also includes evaluating the use model to determine the performance of the at least one product feature of the product and modifying the product sub-model in response to the performance of said product feature and reperforming the steps of interacting and combining the models in the use model and evaluating the use model to determine performance of the at least one product feature.

In another embodiment, the method also includes reperforming the step of modifying the product sub-model until desired performance of said at least one performance feature is obtained to design the product.

Other objects and features of the present invention will be in part apparent and in part pointed out hereinafter.

BRIEF DESCRIPTION OF THE DRAWINGS

FIG. 4 is a perspective representation of a volume mesh model of the representative wearer shown in FIG. 3;

FIG. 5 is a perspective representation of a volume mesh model of a pelvis and femurs of the representative wearer;

FIG. 13 is a top plan view of a representative product, partly broken away to show internal construction;

Figure 1:
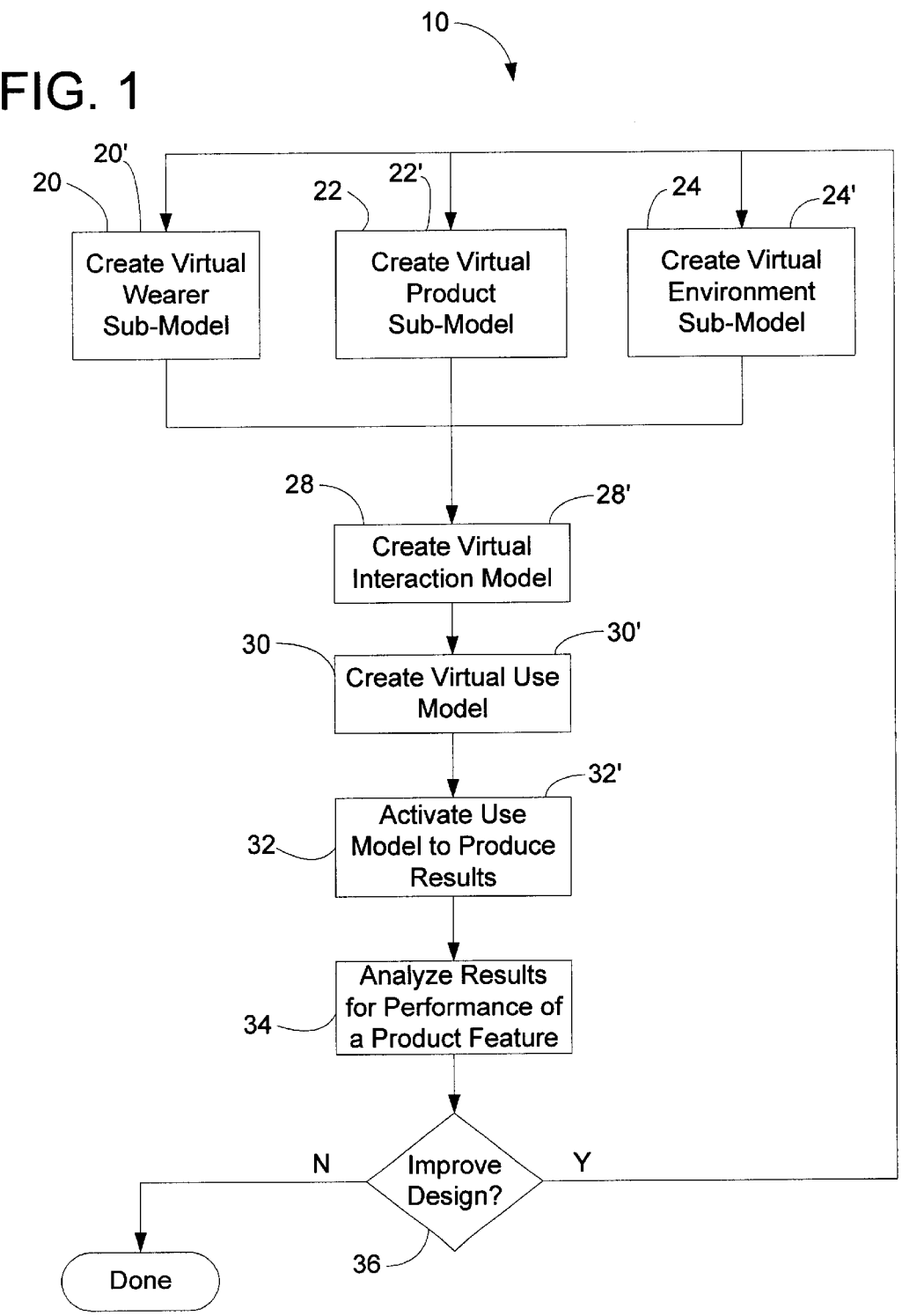
FIG. 1 is a flow diagram showing a method of evaluating and designing a product for use on a body.

Appendix 1 provides an example of input files for an example using the method to evaluate a diaper.

Appendix 2 provides an example of input files for an example using the method to evaluate a feminine care pad.

Corresponding reference characters indicate corresponding parts throughout the views of the drawings.

DEFINITIONS

"Body fit" is the relationship between a body and a product, and may also include the influence of the environment on the body and product.

"Constraints" may include forces, internal pressure, and limits to displacement at selected nodes.

"Contact constraints" define how components interact with each other such as by including specifications dictating or restricting the relative locations or contact surfaces of a model or sub-model and assigning frictional or thermal characteristics when surfaces meet.

"Kinematic constraints" define specifications dictating or restricting the motions of a model or sub-model.

"Instruction" defines how parts of the different sub-models interact with each other.

"Material properties" define the characteristics or parameters of a modeled material and may include the elastic modulus, Poisson's ratio and the like. For example, a user can select mechanical properties to simulate fabric, nonwovens, elastics, bone, muscle, body fat, tendon, etc.

"Product features" are measurable features of a product used to evaluate or design the product, such as stress, force vectors, contact pressure, curvature of a surface, deformation, density profiles, etc.

DETAILED DESCRIPTION OF THE PREFERRED EMBODIMENT

Referring now to the drawings and in particular to FIG. 1, a method, generally indicated by reference numeral 10, of designing and/or evaluating a product for use on a body, is shown. The method 10 is used to develop a preferred product configuration using a computer-based virtual product development and testing system. When used herein, examples of specific equipment, software, products, and wearers are for illustrative purposes, and other types of these items may be used without departing from the scope of the present invention. In one embodiment, the method 10 includes creating a virtual wearer sub-model 20 at step 20' and creating a virtual product sub-model 22 at step 22'. An environment sub-model 24 may also be generated at step 24' so that environmental factors affecting the product or the wearer may also be used in designing or evaluating the product. Information used to create the sub-models 20, 22 and 24 can be obtained from product studies, databases, input from customers, or other sources of product, wearer or environmental data. Numerical method analysis is used to transform the modeling solution of complex interaction between the wearer sub-model 20 and the product sub-model 22 into a system of algebraic equations. Any of the several methods of conducting numerical method analysis known to those skilled in the art may be used. Preferably, finite element analysis (FEA) is used, however, other methods such as finite difference scheme (FDS), boundary element method, minimax methods for parameterized forms, neural network schemes, or cellular automata can also be used. Generally, FEA simplifies the problem into a finite number of unknown fields, sub-divides the region to be analyzed into elements, and expresses each unknown field in terms of assumed approximating functions within each element. Each geometric sub-model is divided into small sections called finite elements through a process referred to as meshing, with a number of nodal points, or nodes, defined at intersections of adjacent elements in the mesh. Meshing is performed using conventional software. Constraints and material properties are then applied to each element of the meshed structure. For example, a user can select mechanical properties to simulate fabric, nonwovens, elastics, bone, muscle, body fat or tendon. As known to those skilled in the art, the types of analysis on the meshed model may include static linear analysis, dynamic non-linear analysis, stability analysis, fluid flow analysis, or heat transfer analysis.

Instructions defining how the wearer sub-model 20, the product sub-model 22 and the environment sub-model 24 interact are introduced in an interaction model 28 created at step 28'. The sub-models 20, 22 and 24 and the interaction defined by the interaction model 28 are then combined to create a virtual use model 30 at step 30' simulating the use of the virtual product sub-model 22 by the virtual wearer sub-model 20. The use model 30 calculates the forces, deformations and stresses caused by movement and interaction between the virtual wearer sub-model 20 and the virtual product sub-model 22 using FEA analysis to solve the solutions for the algebraic systems of equations using conventional FEA software to produce simulation results 32 at step 32'.

The results 32 of the use model 30 are analyzed at step 34 to evaluate the performance of body and/or product features embodied in the virtual sub-model 20, 22 such as when positioned on a virtual wearer and exposed to typical movements or forces. The analysis evaluates the performance of at least one body and/or product feature of the product and/or wearer body. As will be explained in more detail below, body and product features are analyzed to better understand the product structure prior to developing and manufacturing a prototype. For example, two possible product features that may be measured and analyzed are a stress and a strain field. The stress or strain fields are analyzed to determine if the stresses or strains are within desired parameters. If the desired performance level is not achieved, or if additional testing is desired, the analyzed results can be used at step 36 to redesign the virtual product by modifying the characteristics of one or more of the of the sub-models 20, 22 and 24 or the interaction model 28 in order to modify the properties that affect the performance of the body and product features. A user may decide at step 36 to modify the sub-models, or a software program may perform an iterative process to obtain results 32 within a specified range of values. Alternately, the user may decide to modify the sub-models after completing the interaction model at step 28' or the use model at step 30'. After modifying one or more characteristics of the sub-models 20, 22, 24 or the interaction model 28, the steps of running the interaction model 28 and the use model 30 and to obtain new results 32 are performed. The results 32 are again analyzed at step 34 to evaluate the new design. A user may also perform the method 10 using several sub-models 20, 22 and/or 24 having different parameters to perform a controlled set of experiments. For example, sub-models can be created with high and low values for desired parameters and tested. The user then analyzes the results 32 of the multiple runs and based on expertise, statistical analysis, or other decision-making factors, select suitable parameters. It is contemplated that the user may perform the method 10 using any combination of sub-models, for example, creating several product sub-models 22 for use with a wearer sub-model 20 or several environmental sub-models for use with a wearer sub-model. Once acceptable or optimum performance levels for the performance features are determined, the product sub-model 22 can be used as an aid in designing a prototype of the product or specific components of the product.

The method of the invention can be used to design and evaluate any product positioned on a body and particularly a product worn on the human body. For purposes of describing the method and system, the invention is described hereinafter primarily with reference to two personal care absorbent products, specifically a feminine care pad and a diaper. However, it is understood that the method and system may be applied to design and evaluate other wearable articles, such as for example incontinence articles, training pants, facemasks, shoes, and clothing, as well as other products such as medical bandages, medical drapes, jewelry and the like without departing from the scope of this invention.

The Virtual Wearer Sub-model

The computer-based virtual wearer sub-model 20 is a model of a body in a form that can be used for computer simulation. The wearer sub-model 20 preferably defines a deformable "body", such as a person's torso, created to evaluate a product to be worn on the body defined by the product sub-model 22. Alternately, the wearer sub-model 20 can be defined as a rigid body or other object. Preferably, the wearer sub-model 20 is a model of a representative wearer of the product to be designed and evaluated. In one embodiment, the virtual wearer sub-model 20 defines a solid shape corresponding to a representative wearer of the product having mechanical and surface properties. The representative wearer is determined from available usage, demographic, and/or anthropometric data. Although any set of criteria can be used to define this wearer, preferably the criteria defines the three-dimensional surface topography of the wearer, or may include height, weight, and waist, hip, and thigh circumference measurements for the wearer.

Figure 2:
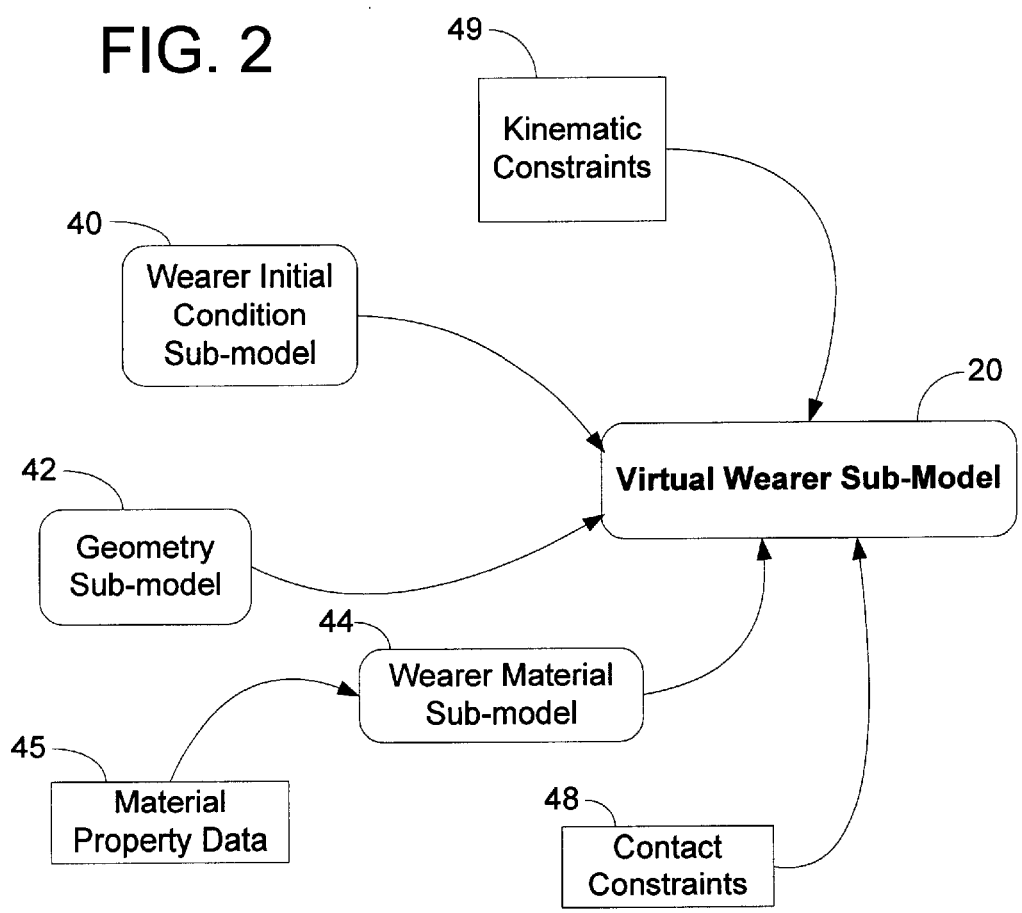
FIG. 2 is a flow diagram showing steps of creating a wearer sub-model for the method of FIG. 1.

As illustrated in FIG. 2, the virtual wearer sub-model 20 includes various sub-models defining information about the typically simplified representation of the wearer. The wearer sub-model 20 includes a wearer initial condition sub-model 40. The wearer initial condition sub-model 40 includes any specified condition that is present at a time selected as the beginning of the event to be modeled. Examples of such initial conditions include the temperature of the body or whether muscles modeled by the model are flexed.

The virtual wearer sub-model 20 includes a geometry sub-model 42. The geometry sub-model 42 includes specifications of the one dimensional (1-D), two-dimensional (2-D), or three-dimensional (3-D) shape and dimensions of the wearer components as well as the position and orientation within a reference frame. In one embodiment, the geometry sub-model 42 includes coordinates of 3-D surface patches describing the exterior shape of the wearer and any internal components to be modeled. For example, the geometry sub-model 42 may include 3-D coordinates relating the location of a hip joint to a point on the surface of the wearer.

The wearer sub-model 20 includes a wearer material sub-model 44. The wearer material sub-model 44 receives material property data 45 for the wearer to be modeled. The material property data 45 may include information such as the measured, modeled or estimated material characteristics or parameters of the representative wearer. For example, the material property data 45 may include information related to the elastic modulus, Poisson's ratio, or density, such as density of bone or soft tissue, of the wearer. The wearer material sub-model 44 defines the intrinsic (measured or estimated) material behavior of the material property components. For example, soft tissue is modeled using a hyperelastic material model to describe a non-linear stress versus strain relationship and incompressibility.

The wearer sub-model 20 also includes contact constraints 48 that define how wearer components interact with each other. The contact constraints 48 include specifications dictating or restricting the relative locations or contact surfaces of the wearer or portion of the wearer and assigns frictional or thermal characteristics when surfaces meet. The contact constraints 48 include whether the components are bonded together or are free to slide with respect to each other. For example, the exterior surfaces (skin) of the wearer may touch but may not penetrate other surfaces. Preferably, the wearer sub-model 20 defines a representative wearer that is deformable with realistic mechanical properties. The sub-model 20 can account for significant variation in mechanical properties with location, such as inner thigh vs. mid back, and natural contours or overall shapes. The wearer sub-model 20 should include sufficient definition to allow the product to "hang" on natural points on the body (e.g., a diaper is held up by the hips). The wearer sub-model 20 also includes kinematic constraints 49 dictating or restricting the motions (translational or rotational) of a wearer or portion of the wearer. Some examples of such kinematic constraints 49 are the head of the femur is not allowed to translate with respect to the acetabulum, and the rotation angle of the hip may be limited to, for example, 45 degrees. The wearer sub-model 20 should balance the need to have realistic anatomical features with the need for appropriate model simplicity.

Figure 3:
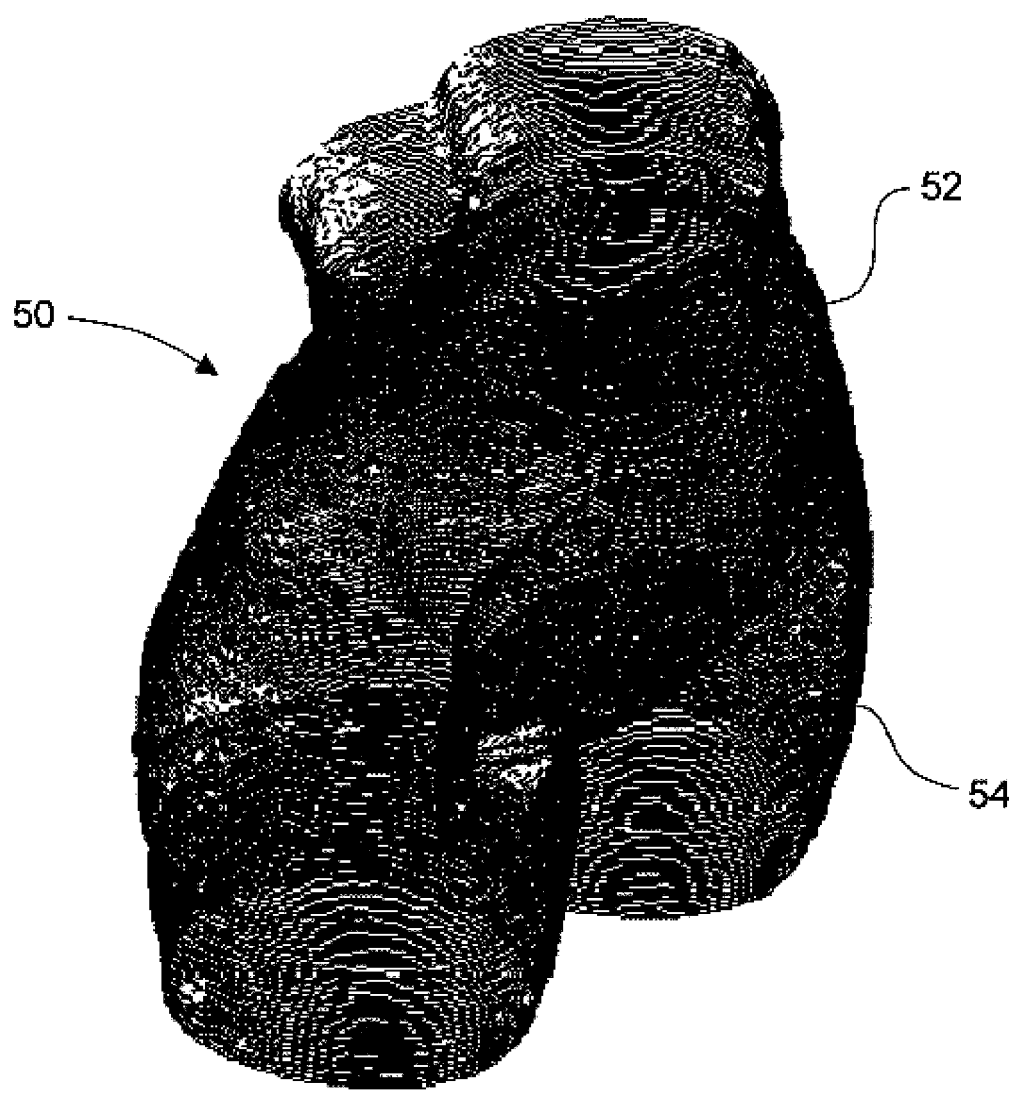
FIG. 3 is a perspective representation of a point cloud model of a representative wearer.

The virtual wearer sub-model 20 is created from a surface point cloud of the representative wearer as indicated generally by reference numeral 50 in FIG. 3. Point cloud data includes a series of points in 3-space that define the surface of an object or body and are generated from various digitization or scanning technologies as is known in the art. In one embodiment, the surface point cloud 50 is obtained from a database containing surface point clouds of persons of various physical sizes. Although any available database or source of surface point clouds can be used to obtain the surface point cloud 50 of the wearer, in one embodiment the data is obtained for an adult wearer from the well known, commercially-available Civilian American and European Surface Anthropometry Resource database collected by the U.S. Air Force commonly known as the CAESAR database (information available at
http://www.hec.afrl.af.mil/cardlab/caesar/index.html).

If the method 10 is used to evaluate or design a diaper, a point cloud of a torso is obtained from a mannequin model of a small-size infant. It is desirable to use a surface point cloud 50 of a pose with an unobstructed view of a region of interest on the body to be modeled. FIG. 3 illustrates a pose of a standing pose of the subject used for evaluating a feminine pad. In one embodiment, in order to reduce the calculational complexity of the model, only the portion of the body in the vicinity of the region of interest is modeled. For example, the wearer sub-model 20 is used in the design of a feminine care pad. In this example, the lower torso 52 and upper legs 54 of the representative wearer are modeled, as they are the body portions that most strongly influence the performance of the product described herein. However, one skilled in the art will understand that any portion of the body may be considered a region of interest depending on the product being designed or evaluated.

Referring now to FIG. 4, a volume mesh model 56 of the wearer's torso geometry is generated from the surface point cloud 50 of FIG. 3. As shown in this example, the volume mesh model 56 defines the surface of the torso 52 and upper legs 54 with a discretized representation of adjacent sections with interconnected nodes. In one embodiment, a watertight volume is generated from the point cloud data using methods known to those skilled in the art. It is desirable to create a "watertight" network of surface patches enclosing the representative wearer volume. The surface model may be subsequently converted to a solid model using appropriate methods specific to the software being used as is known to those skilled in the art. The solid model representation of the wearer may be descretized or meshed using suitable meshing software. Any suitable combinations of geometry manipulation or meshing software can be used to convert the surface point cloud 50 into a volume mesh 56, such as I-DEAS® meshing software from EDS of Plano, Texas, or Geomagic® geometry manipulation software from Raindrop Geomagic of Research Triangle Park, N.C.

Typically, surface point cloud data inherently contains gaps and distortions resulting from the scanning procedure used to produce the surface point cloud 50. During the mesh generation process, these gaps are filled in and distortions removed. For example, the CAESAR data was obtained by laser scan of a partially clothed person. Therefore, this procedure cannot generate surface point cloud data of hidden regions covered by clothing. The CAESAR database lacks detail in the relevant perineal region of the subject due to the subject's legs being almost closed in the standing position. Accordingly, the labia region and other regions altered or hidden by the clothing are filled in. If needed or desired, more detailed data for the hidden regions can be generated. The enhancement of the raw surface data is done to isolate and carefully define the area of importance. Although any area can be isolated and defined, in this example, the torso region is isolated and key surface features such as areas of high curvature are carefully defined in the volume mesh model 56.

As depicted in FIG. 5, the internal structure of the torso is also modeled. Previously, a foam torso test stand has been used to physically test products. In one embodiment, the foam torso test stand's internal components are modeled rather than actual human anatomy to simplify the modeling effort and to allow for direct qualitative comparison between virtual models and test stand data. Starting from the triangular-based volume mesh (see FIG. 4) of the torso and a triangular-based volume mesh of internal components such as a pelvis 57 and femurs 58 as illustrated in FIG. 5, triangular-based volume meshes are created to complete the volume between the components that will be filled with solid elements. Thus, disjoint legs are constructed in the same fashion with pivot points 59 located at approximate hip joint locations 60 to allow for realistic leg closure and fore-aft articulation.

The next step in the simulation process involves adding detail to and refining the user mesh from a coarse mesh to a fine mesh (grid) size if needed. The tissue properties of the representative wearer are then applied to the volume mesh model 56 in the virtual wearer sub-model 20 with the material property data 45. In one embodiment, tissue properties for bone, muscle, fat, and skin are obtained. In another embodiment, bone and bulk soft tissue (lumped properties for muscle, fat, and skin) are modeled. The tissue properties may be obtained from literature and/or test data for use with the wearer sub-model 20. However, one skilled in the art will understand that other suitable tissue properties can be used and any appropriate method used to obtain them. In one embodiment, a softened layer simulating surface fat and muscle is bonded to a rigid substructure to allow for compliance in the torso for later installation of the virtual product sub-model 22.

Figure 6A:
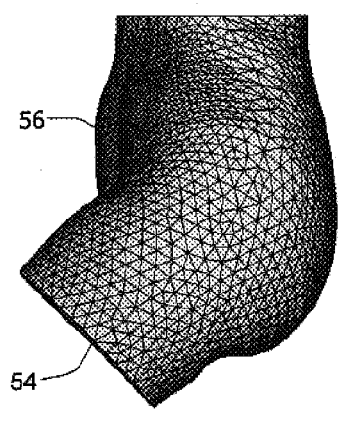
FIGS. 6A–C are perspective representations of a finite element model of the representative wearer illustrating fore/aft articulation.
Figure 6B:
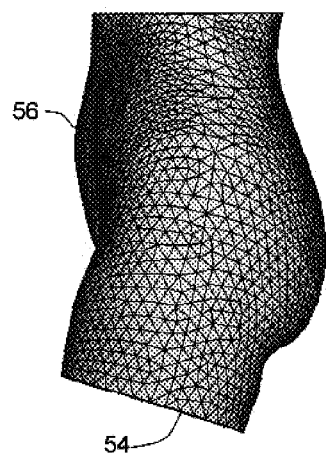
Figure 6C:
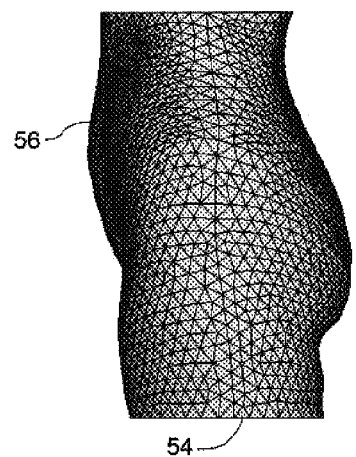
Figure 7A:
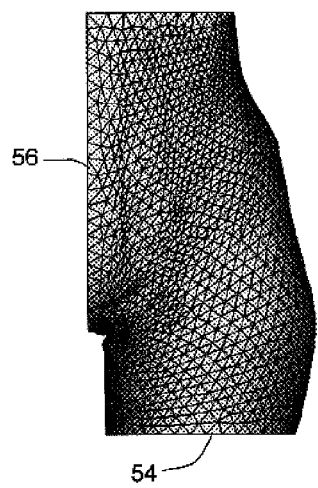
FIGS. 7A–C are perspective representations of a finite element model of the representative wearer illustrating leg closure articulation.
Figure 7B:
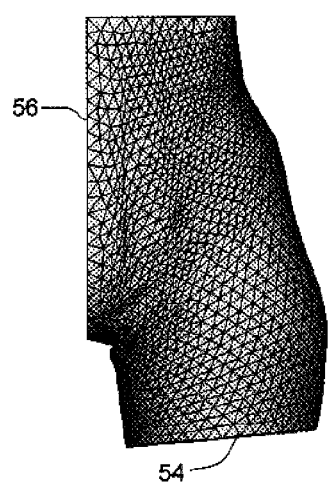
Figure 7C:
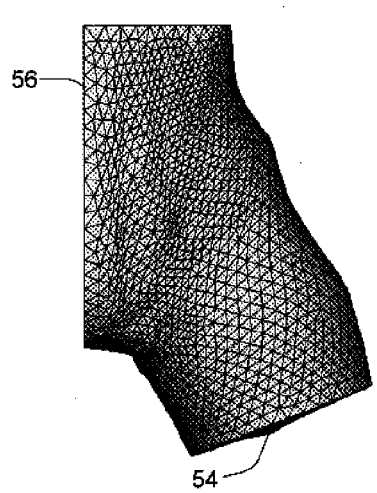

The volume mesh model 56 and the tissue properties are combined to create a finite element model using suitable software. Although any suitable finite element software can be used for the modeling, the process described herein uses the ABAQUS®/Explicit finite element software, such as Version 5.8, 6.2 or 6.3, commercially available from Abaqus, Inc. of Pawtucket, R.I. Alternately ABAQUS®/Standard finite element software is used. It is desirable to give the finite element model an initial undeformed and unstressed shape in the wearer initial condition sub-model 40. For example, in the feminine pad embodiment, a position approximately halfway between a sitting position and a standing position with the legs slightly spread is desirable. This is to mimic the construction of a physical mannequin torso. This initial position allows the finite element model to be moved into either a sitting or standing position without generating excessively distorted elements within the model. The upper legs 54 can also be articulated fore/aft as illustrated in FIGS. 6A–C, or spread through reasonably large angles as illustrated in FIGS. 7A–C.

The Product Sub-model

Figure 8:
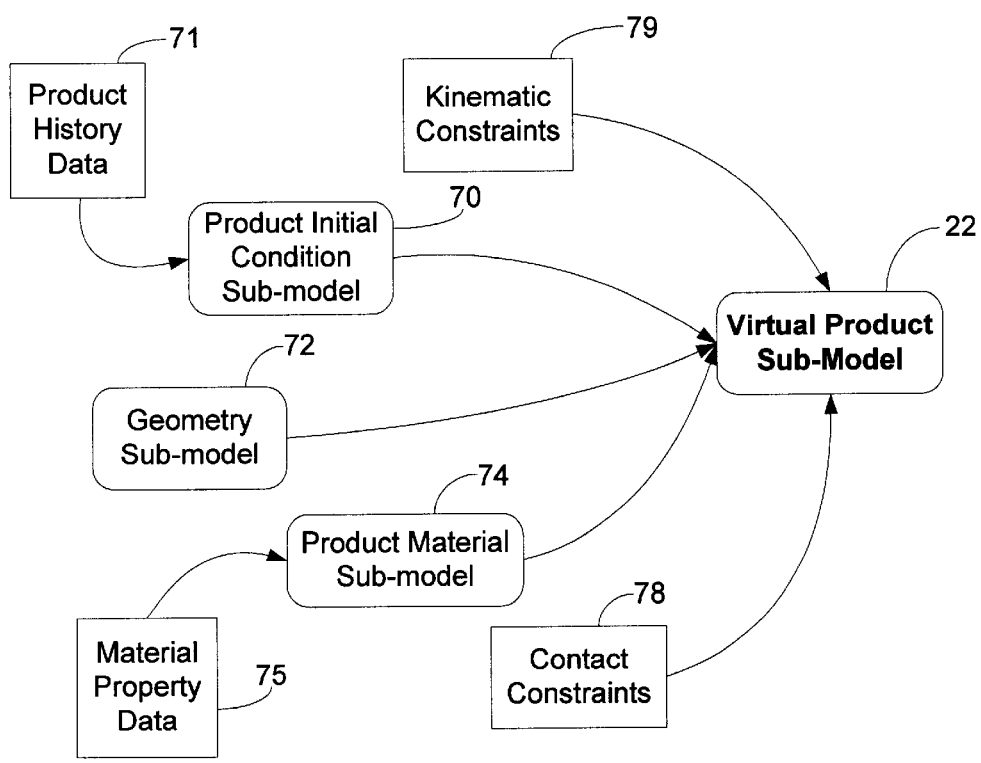
FIG. 8 is a flow diagram showing steps of creating a product sub-model for the method of FIG. 1.

FIG. 8 illustrates the creation of the product sub-model 22 of FIG. 1. As will be understood by those skilled in the art, the product to be modeled is selected based on the product desired to be developed and evaluated using the virtual model method 10. In one embodiment, the product sub-model 22 simplifies the product into a form having a solid shape with selected mechanical and surface properties so that the model can be placed in simulation. The computer-based virtual product sub-model 22 is preferably created as a three-dimensional definition of a desired product with a conventional Computer Aided Design (CAD) system. Although any suitable computer drawing tool can be used to represent the product, the example described herein uses AutoCAD® computer drawing software from Autodesk, Inc. of Sausalito, Calif. and Solid Works® from SolidWorks, Corp. of Concord, Mass.

As illustrated in FIG. 8, the virtual product sub-model 22 includes various sub-models defining information about the typically simplified representation of the product. The product sub-model 22 includes a product initial condition sub-model 70. The product initial condition sub-model 70 includes any specified condition from a product data history 71 that is present at a time selected as the beginning of the event to be modeled obtained. Examples of such initial conditions include the initial temperature of the product or initial stress conditions, such as prestressing. For example, elastic in the diaper may be prestressed (stretched) when attached to a cover. The product sub-model 22 may undergo an annealing process to artificially force the accumulated stresses and strains in the product or a portion of the product to be zero while maintaining a specified position.

The product sub-model 22 includes a product geometry sub-model 72. The product geometry sub-model 72 includes specifications of the 1-D, 2-D, or 3-D shape and dimensions of the product components as well as their position and orientation in a reference frame. For example, in one embodiment, the geometry sub-model 72 includes CAD drawings, solid models, thickness of a layer, embossing lines, and macroscopic absorbent pad topology.

The product sub-model 22 includes a product material sub-model 74. The product material sub-model 74 is a representation of the intrinsic (measured or estimated) material behavior of the product components. The product material sub-model 74 receives product material property data 75 for the product to be modeled. The material property data 75 may include information such as the measured, modeled or estimated material characteristics or parameters of the representative product. Material property data 75 may be obtained from preexisting databases or through testing. The material property data 75 may include information related to the elastic modulus, Poisson's ratio, density of product components, shear modulus, bulk modulus, yield stress, and/or elongation at yield of the product. For example, the product material sub-model 74 may use a linear elastic model, a hyperelastic model, or a viscoelastic model to describe the stress and strain behavior, degree of compressibility, and time dependency in the product material. It is understood by those skilled in the art that some material properties are dependent on the "in-use" conditions of the product material. For example, the material properties of some product materials, such as elastic or elastomeric materials and adhesives may be dependent on such conditions as the product temperature or body temperature of the wearer, the relative humidity, the percent elongation, material deformation, and the like. Preferably, where material properties are dependent on the in-use conditions, material property data 75 specific for the modeled conditions are used. Where the material properties are not substantially dependent on the typical conditions or where it is desired to simplify the complexity of the sub-model, more generic material property data 75 may be used.

The product sub-model 22 also includes contact constraints 78 that define how product components interact with each other. The contact constraints 78 include specifications dictating or restricting the relative locations or contact surfaces of a product or portion of the product and assigning frictional or thermal characteristics when surfaces meet. The contact constraints include whether the components are bonded together or are free to slide with respect to each other. For example, contact constraints 78 may include forced bonding of product layers, such as a liner and a surge layer, at their interface with a no slip/no separation condition, or engagement of diaper fasteners.

The product sub-model 22 also includes kinematic constraints 79 which include specifications dictating/restricting the motions (translational or rotational) of a product or portion of the product. Some examples of such kinematic constraints 79 are fixed positions of the mid diaper back during application of the diaper.

Figure 9:
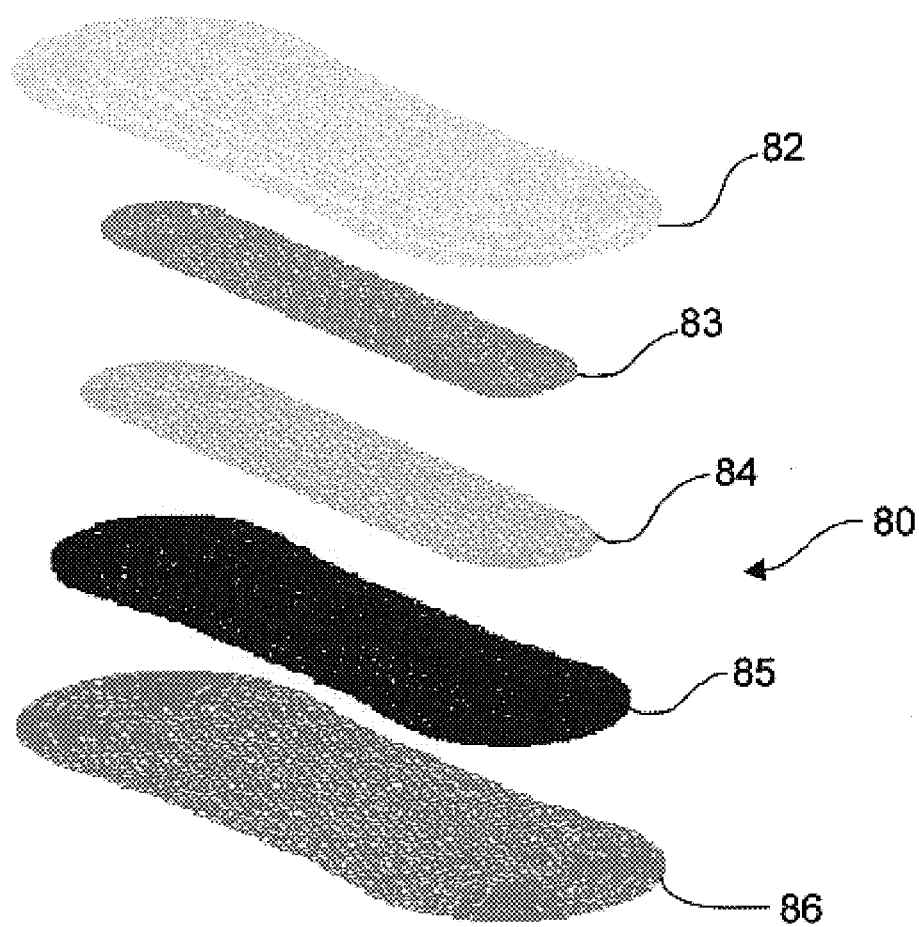
FIG. 9 is a perspective representation of a finite element model of the representative product.

In one embodiment illustrated in FIG. 9, a product, generally indicated at 80, representative of a feminine care pad is generated. The feminine pad product sub-model 22 comprises five layers 82–86 of different materials. The top layer 82, defined as the layer closest to the torso during use, is the cover and is modeled with shell elements. The second layer 83 is a thick distribution layer modeled with solid elements. One skilled in the art will understand using shell elements or solid elements to model different layers. The third layer 84 is a thin fluid transfer layer modeled with shell elements. The fourth layer 85 is a thick shaping layer modeled with solid elements. The bottom layer 86 is a thin baffle layer modeled with shell elements.

Mesh density may be increased, if desired, in selected localities to improve both the modeling accuracy and the fidelity of the finite element analysis in a region of interest. Similarly, the number of layers may be reduced and the modeling of layer interaction may be simplified to reduce time required for analysis, if such simplification is not detrimental to accuracy for a particular simulation, such as when layer interaction is of secondary importance. The complexity of the mesh (number, size, and shape of elements) is a balance between the needs to reduce computational analysis requirements and to provide good resolution into the analysis. Contact between the various layers 82–86 is accounted for initially with a tied contact pair option available in the modeling software. In an alternate embodiment, this accounting can be modified to permit slippage between layers 82-86 that are not bonded in the actual product as defined by the contact constraints 78.

Mechanical properties of the various materials and components of the product 80 are obtained and defined in the material property data 75 to be used in the product sub-model 22. Although any suitable mechanical properties could work, the properties used herein include stress and strain relationships, Poisson's ratio, density and friction properties. These properties are obtained from estimates, measurements, and literature references on the individual components, the product used, or similar products.

The product and properties are combined to create a finite element model of the virtual product sub-model 22. Although any suitable finite element software can be used for the modeling, the software package used herein is ABAQUS®/Explicit. The product sub-model 22 can account for multiple layers or components with specific functions (e.g., temporary storage, transport, non-wet feeling) or made from anisotropic materials (e.g., mechanical properties different in x, y and z directions). The product sub-model 22 can account for material properties for individual components vs. lumped aggregate product. Different material models are required for different components (vs. for example treating everything as a simple linear elastic). The product sub-model 22 can account for geometry based on design drawings or specifications and products that are often held in place by adjacent clothing structures. The product sub-model 22 can account for buckling behavior or plasticity that can lead to non-reversible or permanent deformation of the product (for example, once the diaper or pad is squeezed between thighs, it does not return to its initial shape). The product sub-model 22 can account for limited intrinsic drape or preset shaping patterns. Multiple fitting or deformation patterns are possible.

The Environment Sub-model

The computer-based virtual environment sub-model 24 of FIG. 1 describes the interactive elements of the environment that will participate in the virtual use model 30. The environment sub-model 24 includes information about typically simplified representation of the surroundings. Examples of environmental elements that can have an effect on deformation of the product during use include fluids, such as blood, urine, sweat, and other body exudates, external forces, such as from a car seat or a panty, temperature which can change mechanical behavior of elastic and gasketing components, and other environmental factors, such as clothing, a mother's hand, and/or a caregiver's habits. Additionally, packaging and storage conditions can dictate appropriate initial conditions for the simulation. One example of an environment item is a virtual panty sub-model used in the feminine pad embodiment. In order to improve the accuracy of the product sub-model 22, the virtual panty model is added to the product sub-model 22 to aid in application of the feminine pad to the wearer.

Figure 10:
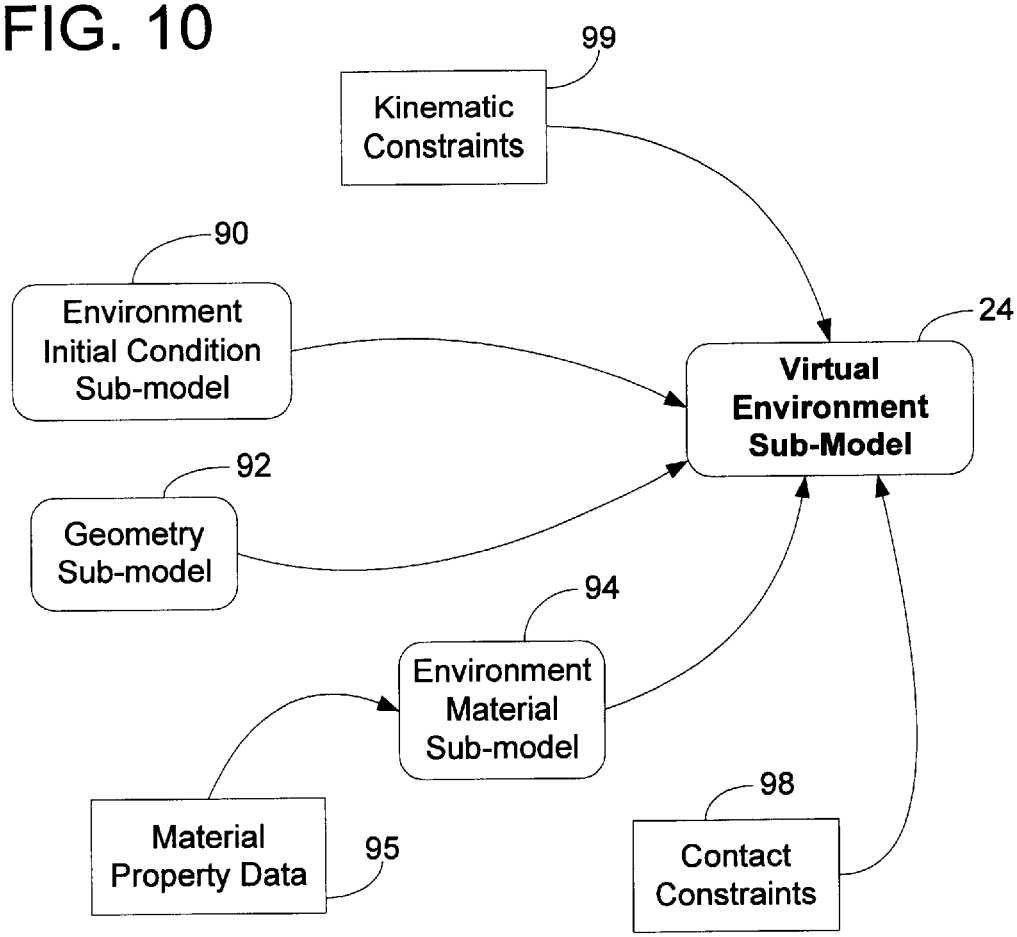
FIG. 10 is a flow diagram showing steps of creating an environment sub-model for the method of FIG. 1.

As illustrated in FIG. 10, the virtual environment sub-model 24 includes an environment initial condition sub-model 90, a geometry sub-model 92, and an environment material sub-model 94. The environment initial condition sub-model 90 includes any specified condition that is present at a time selected as the beginning of the event to be modeled. Examples of such initial conditions are an initial velocity of a caregiver's hand, an ambient temperature, and/or components of the panty that are initially positioned separated from each other.

The geometry sub-model 92 may include specifications of the 1-D, 2-D, or 3-D shape and dimensions of the initial of the environmental objects as well as their position and orientation in a reference frame. For example, in some embodiments, the geometry sub-model 92 includes 2-D or 3-D geometry of a car seat or changing table, a parent's hand, and/or geometry of the panty. The environmental material sub-model 94 uses material property data 95. The material property data 95 may include information such as the measured, modeled or estimated material characteristics or parameters of the environmental objects. For example, the material property data 95 may include information related to the density of the environmental item, such as the density of a car seat or panty. The environmental material sub-model 94 is a representation of the intrinsic (measured or estimated) material behavior of the environmental objects. For example, the environmental material sub-model may use a hyperelastic model to describe the panty material.

The environmental sub-model 24 also includes contact constraints 98 that define how environmental components interact with each other such as by including specifications dictating/restricting the relative locations or contact surfaces of the environmental objects or portion of the objects and assigning frictional, or thermal characteristics when surfaces meet. The contact constraints 98 include whether the components are bonded together or are free to slide with respect to each other. For example, contact constraints 98 may include information as to whether the cushion on the changing table is in contact with the table and can move on the surface of the table, but not pass through the table.

The environmental sub-model 24 also includes kinematic constraints 99 which include specifications dictating or restricting the motions (translations or rotations) of environmental objects. Some examples of such kinematic constraints 99 are a changing table, car seat, infant carrier or other item fixed in space (i.e., not allowed to move), a pad pusher constrained to move in the vertical direction, or edges of different panty materials joined so as to make a single seam move together.

Virtual Interaction Model

Figure 11:
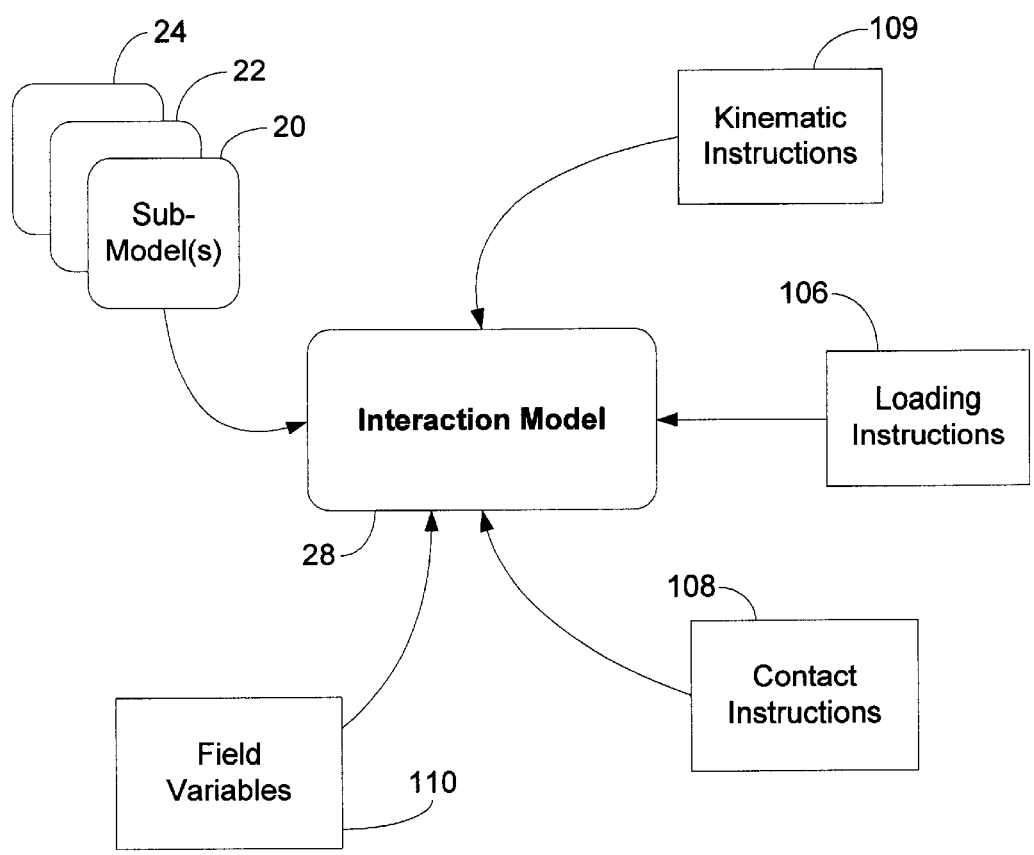
FIG. 11 is a flow diagram showing steps of creating an interaction model for the method of FIG. 1.

Referring now to FIG. 11, the interaction model 28 is intended to establish interactive relationships between the sub-models 20, 22 and 24 and includes both additional constraints as well as dynamic instructions. In one embodiment, the interaction model 28 defines how the product as defined in the product sub-model 22 is applied to the body as defined in the wearer sub-model 22. For example, the interaction model 28 may constrain the product components (from the product sub-model 22) from penetrating the wearer (from the wearer sub-model 20). The interaction model 28 may also specify how the product and body are to move to facilitate the virtual donning of a product. The interaction model 28 may specify the stresses, forces, contacts pressures, displacements, velocities or accelerations (in the product or the body) at a node, along a line or on a surface. Additionally, the interaction model 28 may account for placement of the product on the body which can affect performance. In one embodiment, an external pad pusher is used to apply and position a feminine hygiene pad relative the body, and then removed for the remainder of the run. The interaction model 28 may account for realistic application (in terms of force, location) of the product to the body (vs. another approach, such as an expanding second skin that becomes a product). Additionally, the expected latitude in product placement due to individual preference can be defined in the interaction model 28. The interaction model 28 can force the product into a certain configuration to position the product and then relax to allow the product to reach an equilibrium condition determined by the internal forces of the product. For example, waist elastics on a diaper are forced into a desired position relative the wearer and then the internal forces of the diaper are allowed to move the diaper into an equilibrium position on the wearer.

The interaction model 28 includes kinematic instructions 109 which may include specifications defining the positions and motions (translational or rotational) of the sub-models, such as the wearer walking when the product is in place and applying product and clothing to the wearer. The kinematic instructions may include position/displacement instructions (e.g., the front edge of diaper is displaced by (dx, dy, dz); back edge of diaper is free to move in the x direction but constrained in the y and z directions to dy=dz=0). The kinematic instructions 109 may include velocity vector instructions (e.g., an initial velocity vector is specified on an object initially in motion, the motion can be allowed to decay or maintained using a boundary condition). The kinematic instructions 109 may include acceleration instructions (e.g., an acceleration may be specified at one or more points to facilitate the application of a virtual product).

Additionally, the kinematic instructions 109 may include multi-point constraints (MPC's) (e.g., the points on adjacent seam edges of a panty may have their translational degrees of freedom constrained to be equal—causing them to move together). The kinematic instructions may include equation instructions (e.g., relating one or more degrees of freedom of two or more points by some specified mathematical equation, thus constraining their relative motion). The kinematic instructions 109 may include connector instructions (e.g., a pre-built set of loading and/or kinematic constraints intended to mimic mechanical joints such as a slider or a revolute joint). The kinematic instructions may include damping instructions (e.g., a relation that produces a force opposing motion based on a relative velocity of a component).

The kinematic instructions 109 may include sticking instructions (e.g., no relative motion between surfaces allowed) and sliding instructions (e.g., relative motion allowed, separation of surfaces may or may not be allowed depending on the specification). Additionally, the kinematic instructions 109 may include friction instructions (e.g., mechanism to produce a force opposing motion between surfaces in contact) and lubrication effect instructions (e.g., a means of affecting the friction behavior depending on one or more independently specified values such as degree of lubrication or temperature). Kinematic instructions also define the motion of the wearer throughout the simulation. One to several representational uses and motions of the product sub-model 22 by the wearer sub-model 20 and the forces generated can be modeled in the interaction model 28. The motions defined in the interaction model 28 to be modeled are selected based on the motions a developer desires to model to assist in developing the product. As illustrated in the examples described herein, the type of motions typically selected are everyday motions (e.g., walking, a sit to stand movement, spreading/closing legs, etc.) or motions that cause a performance stress on the product, such as motions that might cause tearing of the product. For example, although any series of motions may result in a positional gush from a feminine care pad, motions performed transitioning from a sitting to a standing position and motions performed when closing the legs resulting in squeezing of the product are particularly useful in evaluating the performance of the product and are modeled. Although any suitable technique can be used to determine the motions of the wearer, one technique used herein is the MotionStar® motion modeling system from Ascension Technology Corp. of Burlington, VT., coupled with the JACK human simulation software from EDS of Plano, Texas to determine the motion. To analyze the motion of the wearer, data is obtained using sensors at certain wearer body points. Although many sensors can be used with the MotionStar system, the analysis described herein uses six sensors. These sensors determine the position and orientation associated with the back of the neck, the back of the waist, the right and left knees, and the right and left feet. The data obtained is interpreted and translated through the JACK software into joint center motion of the bottom vertebrae in the spine, the right and left hip joints, and the right and left knee joints. The motion data obtained is then incorporated into the interaction sub-model 28. Other sources of data for body movement or motion analysis can be utilized, such as data from one of several published sources known to those familiar with the art of motion analysis.

The interaction model 28 includes loading instructions 106 defining pressures, moments or forces, temperatures or other thermodynamic fields acting on the sub-models. For example, the loading instructions may include the parent's hand pulling the diaper fastener with a given force, or gravity. Additionally, the loading instructions 106 may include force (e.g., concentrated load acting on a single point of series of points), pressure (e.g., force distributed over an area) and body force (e.g., the force acting on a body continuum such as gravity or buoyancy).

The interaction model 28 includes contact instructions 108 dictating or restricting the relative locations or contact surfaces of the sub-models 20, 22, 24 or portion of the objects and assigning frictional or thermal characteristics when surfaces meet. For example, the interaction model 28 can define that the product sub-model 22 cannot penetrate the wearer sub-model 20, that clothing modeled in the environment sub-model 24 cannot penetrate the product sub-model 22, and the friction type and value between product sub-model and the wearer sub-model. Additionally, heat source and/or sink factors and the transfer of heat between components in contact can be defined. For example, heat transferred from the wearer sub-model 20 to the product sub-model 22 simulates body heat going into the product. The contact instructions 108 may include contact/surface interactions (e.g., specification of how two or more surfaces or surface representations interact when and while they meet).

The interaction model 28 receives field variables 110 such as field intensity for various physical or fictitious quantities that can affect material properties or potentially other loads or instructions. These field values may correspond to physical or fictitious quantities such as temperature. In one embodiment, the nodal temperatures are specified to facilitate shrinkage/expansion as in stretched elastics. In another embodiment, varying (temperature dependent) material properties are introduced, using temperature as a true or fictitious value. Other field variables may include light intensity, proximity to a magnetic source, intensity of fields generated by electric energy, microwave energy, or ultrasound, a lubrication factor, a relative humidity factor, the skin orientation (i.e., Langer's lines), a local body tissue modulus, material (property) variability, heat transfer factors to/from a heat source/sink, and initial or boundary conditions for field dependent loads. Other field variables 110 may include local (non-uniform) material property (e.g., specifying some areas of the body's local material property), stochastical local variation (local deviation of a property or boundary condition). Other field variables 110 may include the mass fraction or a fraction of a quantity of interest with respect to the total mass of the volume, such as, for example, the mass of fluid in a cubic mm of absorbent material. Additionally, the mass transfer or movement of mass across a defined boundary, typically specified as the flux or mass moving through a unit area can be specified as a field variable.

The Use Model

Figure 12:
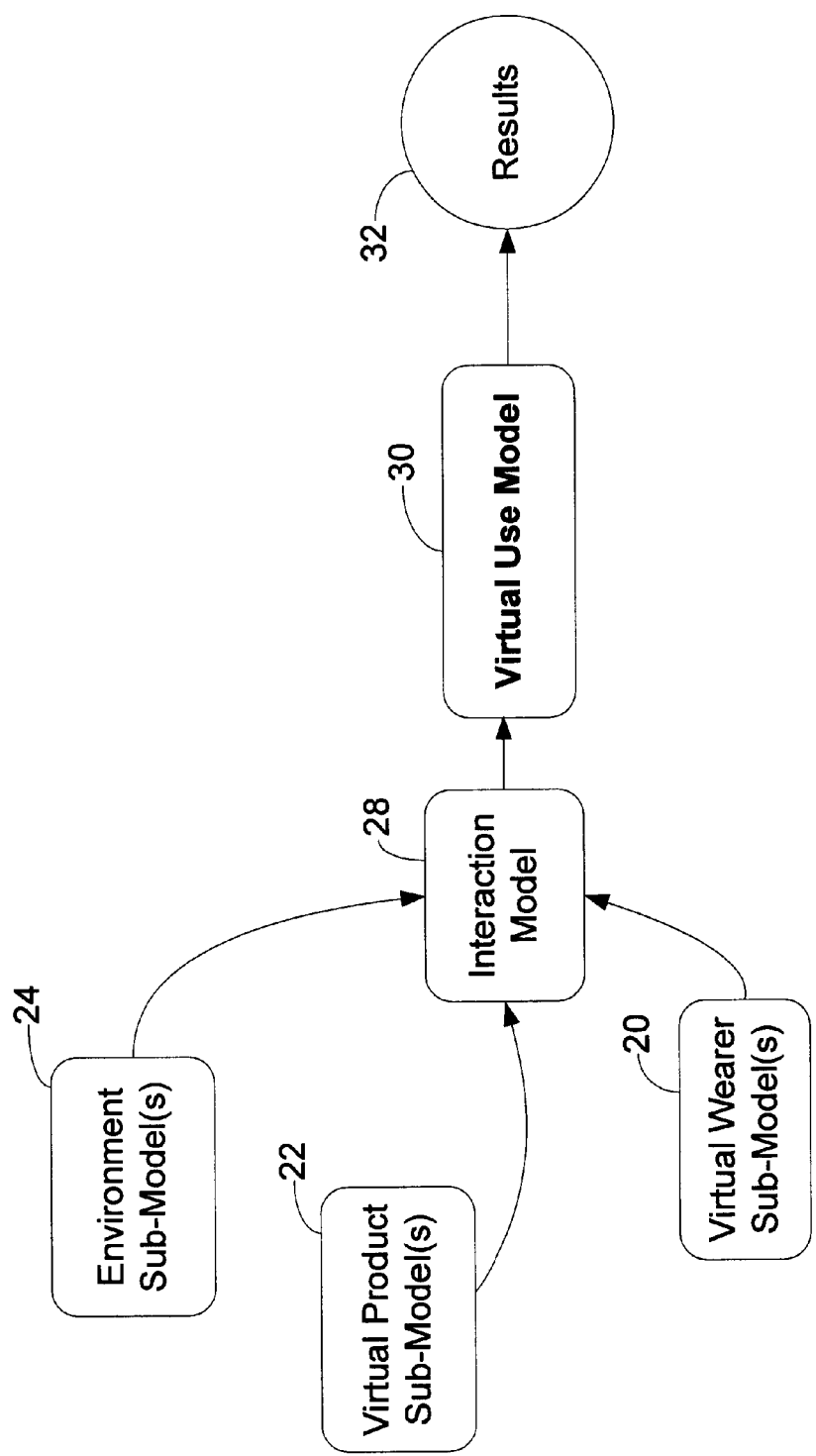
FIG. 12 is a flow diagram showing steps of creating a use model for the method of FIG. 1.

Referring now to FIG. 12, the virtual use model 30 combines and integrates instructions and model definitions from the wearer sub-model 20, the product sub-model 22, the environment sub-model 24 and the interaction model 28, to define a virtual use simulation. The use model 30 calculates or otherwise determines the forces, stresses and strains caused by movement and interaction between the virtual wearer sub-model 20, the virtual product sub-model 22 and the environment sub-model 24 using FEA analysis to produce simulation results 32. Any combination of one or more of the virtual wearer sub-models 20, virtual product sub-models 22, and virtual environment sub-models 24 may be included in the virtual use model 30 as desired for the particular evaluation to be performed or product to be designed. The virtual use model 30 is driven by the instructions provided by the interaction model 28 and is representative of motion induced by the interaction model 28 on the sub-models 20, 22, 24 through an elapse of time. Preferably, the use model 30 calculates the actual forces on the product or the body at a level of mm resolution.

Animations can be produced as an aid in setting up, using and interpreting the models. Animations can display simulation results over time, depicting the model in any desired orientation. The display options may be set to show the entire wearer and product or just that portion of the wearer and/or product that is of interest for a particular result. Some examples of animations used for viewing results are as follows. The animations help to visualize the actual articulation of the torso and the application of the product discussed herein with references to static images. For example, animations can show the product being applied to the torso, followed by leg closure, then by leg stride. Animations can also show the articulation of the torso from a frontal view, a side view, and an isometric view. Animation can also show a coronal cross-section view of the product being applied to the torso. Views of the torso, product, and environmental features, or of the torso and product, or of only the product can be shown. Finally, animation can show a coronal cross-section view of the product being applied to the torso, initially with legs spread, followed by leg closure.

It may be necessary to use various techniques known to those skilled in the art of FEA to enable the numerical methods to operate. For example to prevent element hourglassing, beam elements around the perimeter of the product can be inserted. To prevent long run times due to artificial intertial effects, mass scaling may be used. To prevent overclosure/wave propagation, damping can be inserted. To prevent limited wearer range of motion due to excessive element distortion, the removal volumes of material can be used. To more accurately model the anisotropic elastic material, a homogeneous membrane together with elastic strands can be used. To allow for non-uniform strain between attached elastic components, elastics can be tied to every 3rd node of the product. To provide controlled contraction of elastics, temperature and thermal expansion can be controlled. To control buckling in a certain direction, a pressure such as from an air puff or rigid pusher can be used. To control contact instabilities, the penalty contact method can be used. To reduce non-physical stress buildup (e.g., in the body) annealing protocols can be used to remove stresses and strain. To control the speed versus accuracy and stability, local or global remeshing can be used. These examples are for illustrative purposes. It may be necessary to use some, all, or additional techniques during the performance of this method 10 to control excessive element distortion, propagation of numerical instability and speed versus accuracy issues.

The results 32 of the use model 30 are analyzed at step 34 to evaluate the performance of virtual product. The analysis 34 evaluates the performance of at least one body or product feature of the product and/or wearer body. The response includes details of the product's behavior, driven by interactions with itself and potentially other factors such as a wearer and/or its surrounding environment. The results 32 include the performance of one or more product features related to the fit, comfort or use of the product. Depending on the product to be developed, a number of body or product features can be looked at to determine whether the product will perform satisfactorily under normal use conditions.

The product features analyzed may include one or more of features such as, but without limitation, product stress, product force vectors, contact pressure distribution on the body, curvature of a product surface, product deformation, density profiles, predicted stresses at selected locations of the product, the gaps between the body and the product, the appearance of the product or garments introduced by the environment sub-model when worn by the body, deformation of the body, contact area between the body and the product, the integral of the pressure over the contact area, the contact area between the panty and the product, appearance of the product when in contact with an external article. For the examples described herein, a product developer can examine the contact pressure on the user from the product, which is a factor in determining the product's comfort. It was seen that the contact pressure distribution in the product varied during use, with higher contact pressure regions adjacent the legs, and lower contact pressure regions away from the legs. In addition, density variations in the product provide insight into the absorbent behavior or permeability of the product. Areas of higher density can tend to absorb fluid less rapidly than areas of lower density. Tensile stress within the product is a large factor in determining the integrity of the product. A concentration of tensile stress in a particular region of the product can lead to tearing of the materials in that region. The fit of the product relative to the wearer contributes to the discretion in the use of the product. Also, the shape of the product during use contributes to many of these results including discretion, pressure, and absorbency. Some or all of these and other product features can be modeled and analyzed by the process described herein. A variety of product designs (e.g., shape, size, materials) may be simulated and comparatively analyzed. Less promising candidate designs may be removed from further study.

The fit of the product can be measured using quantitative measurements to define fit. Some measurements include uniform and optimal tension, contact pressure or stress throughout the product or a portion of the product, providing and/or maintaining a desired surface area of coverage during changes in body position, and conformance to the body surface area. Additional measurements can include how the product follows the natural lines of the body, the relative motion between portions of the product and the body, and bunching, twisting or roping of the surface topography of the product. Examples of product features analyzing the fit of the product include product deformation such as can be determined by the measurement of product movement or shift during wear (i.e., during wearer movement) and gaps formed between the product and the body. In some instances, gaps can cause particular products, such as absorbent articles, to have reduced effectiveness. Product stresses can be analyzed to determine the potential for material tears or places that need stretchable material or reinforcement. The force vectors for every element of the diaper may be output throughout the simulation. This type of output aids product developers when investigating different product designs. Specifically, product developers can analyze the forces, noting any large vectors such as those which may cause the product to droop over time. Reduction of large forces may lead to better fit maintenance or a reduction of product failures (i.e., tearing). The product curvature can be analyzed to determine the conformance of the product toward or away from the body. The product strain can be analyzed such as to determine the amount of stretch being used by diaper fasteners. The contact area can be analyzed to determine if the product is covering the entire target surface area of the body. Shape analysis or anthropometric landmark analysis of the wearer can be used to determine fit ranges such as the distance between facial landmarks to determine area for facemask coverage. Additionally, the relative distance between a product feature and a wearer landmark can be analyzed to determine fit such as the droop measured as the distance from the belly button to the top of the product waist.

Examples of body and product features analyzing the comfort of the product include contact pressure distribution on the body and the magnitude of natural body shape alteration caused by product. These features can lead to skin irritation or make the product uncomfortable to wear. The appearance of the product when worn by the body can be analyzed to determine how the product buckles, twists and/or bunches during wearer movement. The contours of the product can be mapped to trace the path on the wearer where the contact pressure is equal to a certain value or range. A thermal analysis can be performed to determine the heat or humidity between the product/wearer as compared to environment.

Examples of product features analyzing the effects of the environment on the product include the appearance of the product such as the discreetness of product during wear. The contact area between the product and any additional garment worn on the body can be analyzed, such as whether the product is in contact with the garment or does a portion of the product hang outside the garment.

Analysis 34 of the performance of the body and product features typically indicates changes that may be made to the product for improved performance. If the desired performance level is not achieved, or if additional testing is desired, the product sub-model 22 is redesigned in order to modify the performance of the product feature. For example, a concentration of tensile stresses in a particular region of the product may indicate that a material or shape change needs to be made in that region. The product developer may also revise the wearer sub-model 20 to revise the body that the product is being evaluated on. Additionally, the environmental sub-model can be modified to account for different environmental conditions. After modifying one or more characteristics of the sub-models 20, 22, 24, the steps of running the interaction model 28 and the use model 30 and to obtain new results 32 are performed. The results 32 are again analyzed at step 34 to evaluate the new design. In this manner, results of a product analysis may be fed back into the product design process in an iterative manner until the design of a product meets whatever goals are set out for it. The product developer may decide at step 36 to modify the sub-models, or a software program may perform an iterative process to obtain results 32 within a specified range of values. Once acceptable or optimum performance levels for the performance features are determined, the product sub-model 22 can be used as an aid in designing a prototype of the product or specific components of the product.

The process may also be repeated using different products, wearers, and uses. Thus, virtually any combination of a wearer and a product of clothing or other articles which are used on the body may be modeled. For example, the entire modeling process may be repeated for a representative baby using a particular diaper design. In another example, a representative adult incontinence product user may be modeled using a particular adult incontinence product. In another example, a representative child may be modeled using a product of clothing such as pajamas. In each of these, the same iterative product development process may be followed to develop a product that meets any initial performance goals.

Correlations can be made between simulated or virtual data and in-use wearer data to establish product shaping, body fit and comfort targets for multiple product platforms, improving product fit with the body and wearer perception of wearing comfort and security. Proposed improvements can be screened virtually to ascertain if the product achieves desired performance of product features related to, for example, absorption of the product, gapping between the product and the wearer, contact pressure between the product and the wearer, proximity of the product to the wearer, and/or relative orientation of surfaces of the product to gravity. The performance of body and product features can be compared against wearer preferences for fit and comfort.

Example 1—Diaper Embodiments

Embodiment 1a

Figure 13A:
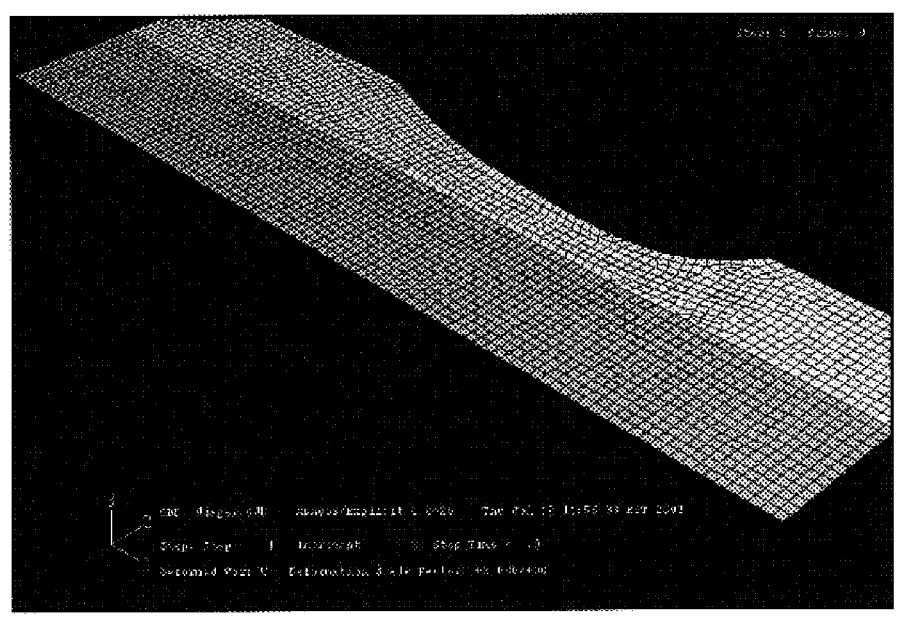
FIG. 13A is a perspective simplified representation of the product of FIG. 13 according to one embodiment of the method.
Figure 14:
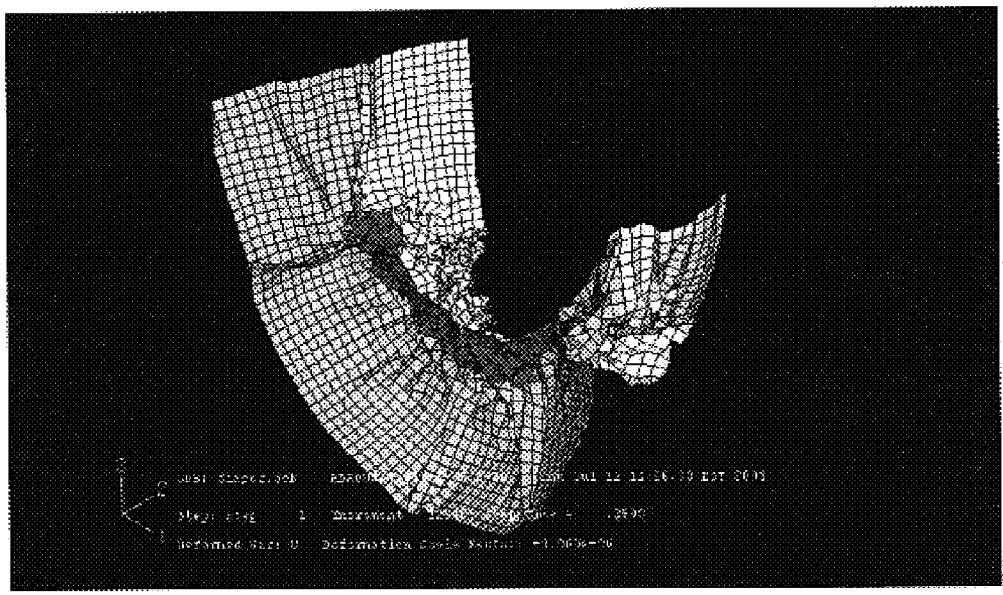
FIG. 14 is a perspective representation of an example of the product in a simulated final position.
Figure 15:
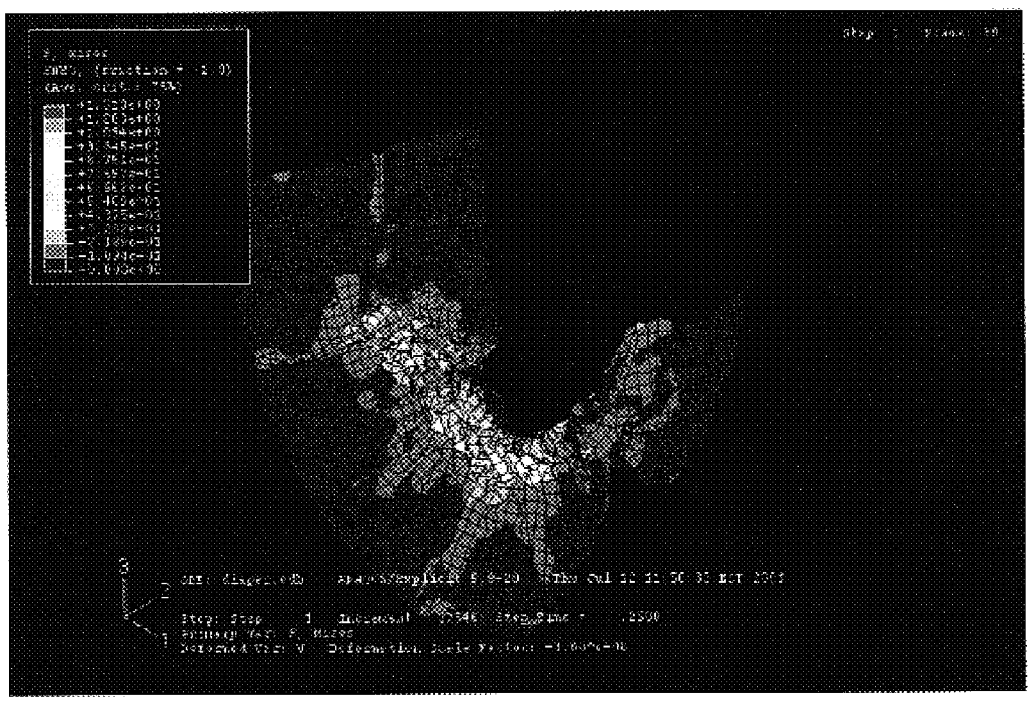
FIG. 15 is a perspective representation of the stresses (Mises stresses) in the product.

The first diaper embodiment described herein is a product only model used to evaluate deformation and stresses around the leg and containment flap elastic regions. FIG. 13 illustrates an exemplary diaper, indicated generally at 111, with typical fasteners and elastics. For example, the diaper 111 has a cover 112, an absorbent body 113, fasteners 114, fastener elastics 115, containment flaps 117 and leg elastics 118. Initially, a plane of symmetry along the long axis of the diaper was implemented to reduce computer run times during the initial steps of development. Later, the plane of symmetry constraint was removed by mirroring the diaper about the plane of symmetry. When the mirroring was implemented, modifications were also made to the loading conditions (i.e., forces necessary to apply the diaper), kinematic instructions, and contact instructions. Appendix 1 provides an example of the input files for the diaper embodiments. Diaper embodiment 1a focused on the leg and containment flap elastics and simulated the diaper being stretched out flat, released, and then allowed to come to a "resting" position. Therefore, the geometry in this phase of the diaper creation was relatively simplistic, and only included detailed material models for the leg and containment flap elastics. The rest of the diaper was modeled as one continuous homogeneous sheet. FIG. 13A shows the diaper in the simulation initial position, held flat and under tension. FIG. 14 depicts the diaper in the simulation final position, with external tensions released and the diaper allowed to relax. Element stresses were also calculated throughout the simulation, and the final stresses (Mises stresses) are displayed in FIG. 15.

The non-woven materials were modeled as shell elements of type S4R (reduced integration quadrilateral shell element). This is a shell element, which is often used for structures in which the thickness is significantly smaller than the other dimensions. The leg and containment flap elastics were modeled as two force members (ABAQUS type T3D2truss elements), which act as rods that can only support an axial force between the two points. They have no resistance to bending. This description is representative of how the leg and containment flap elastics primarily behave, and demonstrates the importance of choosing elements that best represent the behavior of the material they are modeling. Table 1 lists the material definitions and material property data of embodiment 1a of the virtual diaper.

TABLE 1

Material definitions and material property data of the virtual diaper. The units for this model are a standard SI form of N-mm-sec-Mgr. Note: a Megagram is equal to a metric ton.

|  | Element Type | Thickness (mm) | Density (tonne/mm$^3$) | Young's Modulus (MPa) | Poisson's Ratio |
|---|---|---|---|---|---|
| Center Region | S4R | 0.1574 | 9.32*10$^{-10}$ | 7.549 | 0.3 |
| Outer Region | S4R | 0.0574 | 9.32*10$^{-10}$ | 7.549 | 0.3 |
| Containment flap Material | S4R | 0.065 | 1.23*10$^{-9}$ | 29.9 | 0.3 |
| Leg Elastic | T3D2 | 0.1 | 1*10$^{-9}$ | 2 | 0.4 |
| Containment flap Elastic | T3D2 | 0.1131 | 1.1*10$^{-9}$ | 2.82 | 0.4 |

With no external wearer or environment in this simulation, it was necessary to apply a very small pressure (similar to a puff of air) in the negative (3) direction (refer to FIG. 13A for axes orientation). This allowed the diaper to buckle downwards, or away from the body, instead of upwards, or toward the body. To account for the variation in amount of strain between the elastics and the diaper, the elastics were connected to every 3$^{rd}$ node instead of every node. This allowed the elastics to stretch without distorting the diaper elements.

Embodiment 1b

The second embodiment included a more detailed product and a wearer located in a static position. In this model, contact pressures during product application and deformation of the product were investigated. The increased detail in the product included modeling the geometry and properties of an absorbent core, fastener elastic, and a fastener in addition to the leg elastic, containment flap elastic, and containment flap material modeled in embodiment 1a.

Material property data of the updated diaper may be found in Table 2. The elastics (containment flap, leg, and fastener elastic) were modeled as Neo-Hookean hyperelastic materials, which means that the materials are incompressible and show non-linear behavior. To accurately describe the non-linearity in these materials, stress vs. strain data was directly input to the model. All of the elements except the leg and containment flap elastic were modeled as S4Rs. These elements allow a user to represent many types of materials in one element (e.g., a composite shell element). For example, a section may be modeled as having cover and absorbent. Each material in this section will be defined by its own properties, but the materials will not be allowed to "shear" (move back and forth) with respect to one another, but are constrained to move as a unit. Utilizing this assumption allows for faster simulation run times during model development. The leg and containment flap elastics continue to be modeled as T3D2 truss elements, but the material properties were updated to better represent their characteristics.

TABLE 2

Material definitions and material property data for the updated virtual diaper.

|  | Element Type | Thickness (mm) | Density (tonne/mm$^3$) | Young's Modulus (MPa) | Poisson's Ratio |
|---|---|---|---|---|---|
| Absorbent | S4R | 5.0 | 5.0*10$^{-10}$ | 1.0 | 0.1 |
| Containment flap material | S4R | 0.3 | 1.23*10$^{-9}$ | 29.9 | 0.3 |
| Containment flap elastic | T3D2 | 0.01767 | 1.1*10$^{-9}$ | Test stress vs. strain data | 0.5 |
| Leg Elastic | T3D2 | 0.01767 | 1.1*10$^{-9}$ | Test stress vs. strain data | 0.5 |
| Fastener Elastic | S4R | 0.6 | 1.1*10$^{-9}$ | Test stress vs. strain data | 0.5 |
| Fastener | S4R | 1.6 | 1.23*10$^{-9}$ | 29.9 | 0.3 |
| Cover | S4R | 0.15 | 9.32*10$^{-10}$ | 7.549 | 0.3 |

Figure 16:
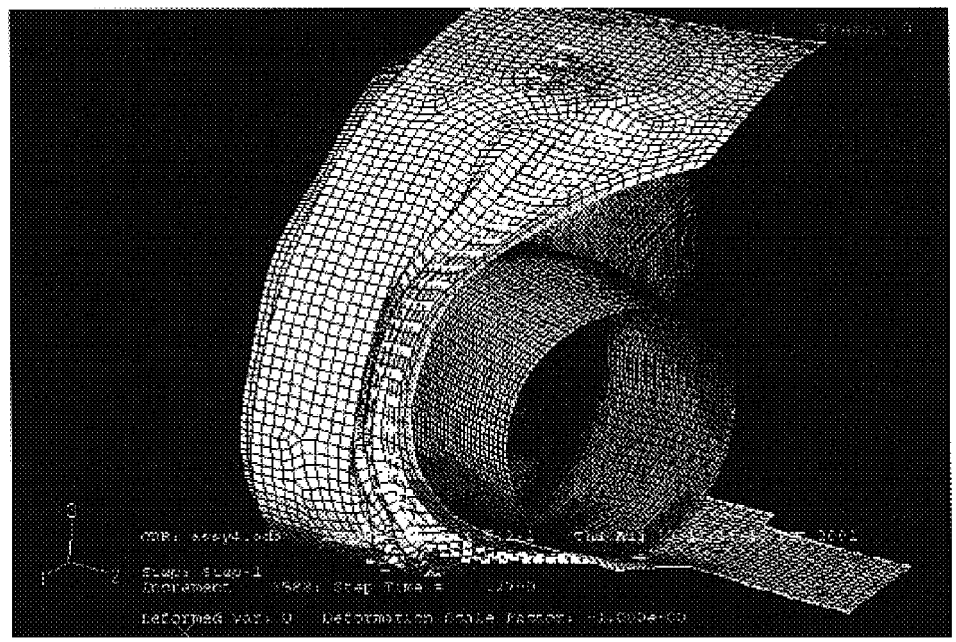
FIG. 16 is another perspective representation of the product applied to the wearer showing placement of the product.

In addition to adding complexity to the diaper, the method of diaper application during the simulation was refined to appear representative of actual diaper application. This included refining the direction, timing, and magnitude of the application forces so that the data is consistent with typical use. FIG. 16 depicts how the diaper is pulled between the legs and then wrapped onto the torso of the body. Deformation of the product and contact between the virtual product and virtual infant during the simulation of application is shown in FIGS. 16 and 17.

A model of a baby's torso situated in the diapering position (e.g., lying down with legs spread) was used for the wearer sub-model. The geometry data for the infant wearer sub-model 20 was obtained from a mannequin model of a small infant. The process used to obtain this data included scanning a mannequin torso to obtain a 3-D point cloud. The point cloud data was then converted into a surface model using Geomagic software. The surface model was then converted into a FEA model using the meshing and model definition features of Abaqus/CAE. This step requires specification of both the geometry and element type (with associated material properties) of the wearer. The elements specified for this virtual wearer were the rigid material R3D4 elements (three-dimensional quadrilaterals). This element type does not require the specification of any material properties. It is used to model the 2-D surfaces of a 3-D rigid body. To make the surface properties more realistic, a softening layer was included above the rigid foundation. The softening layer was specified as a 3 mm thick layer that would fully compress to the rigid foundation at a contact pressure of 0.1 MPa.

Techniques necessary to enable the simulation to operate for this embodiment included changing from the default Lagrange contact algorithm to Penalty contact in order to fasten the diaper ear. This was done to prevent element hourglassing (nonphysical grid distortions, potentially leading to contact problems). Placing 0.1 mm beam elements around the perimeter of the diaper prevented hourglassing elsewhere in the diaper. These elements were given the properties of diaper cover material. To stabilize and better control the rate of contraction of the elastics and the diaper, the initial condition pre-stress in the elastics was removed and replaced with a temperature control. Instead of causing elastic contraction by lessening the pre-stress, an arbitrary temperature lowering is used to contract the elastics. This method provides more control over the rate of diaper deformation and results in a successful and more stable simulation.

Figure 17:
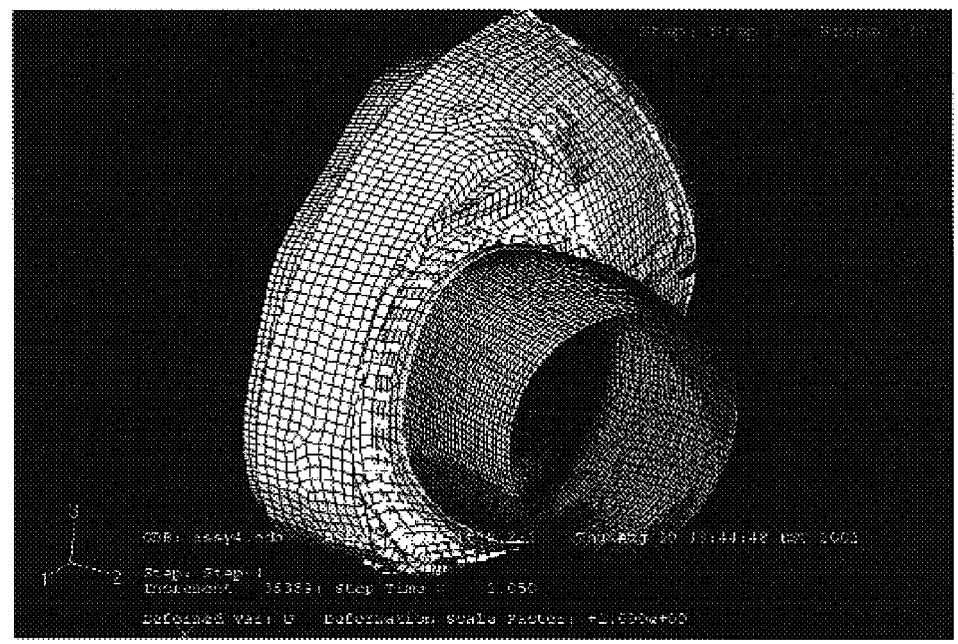
FIG. 17 is a perspective representation of a product according to one embodiment of the method.
Figure 18:
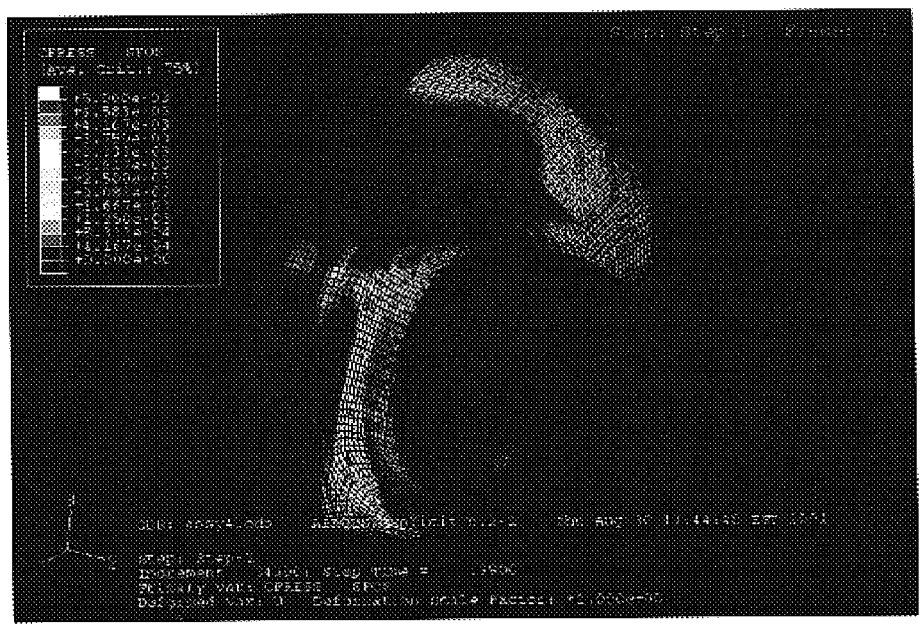
FIG. 18 is a perspective representation of the wearer showing the contact pressure profile between the product and the wearer.
Figure 19:
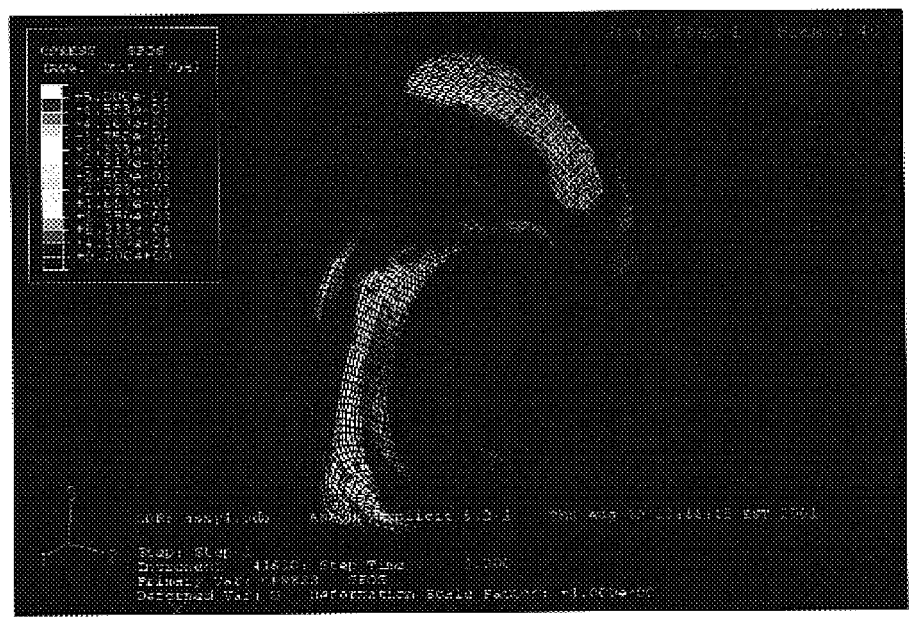
FIG. 19 is another perspective representation of the wearer showing the contact pressure profile between the product and the wearer at a different point during application.

A snapshot from the simulation of applying the diaper to the virtual user is shown in FIG. 17. During this simulation, contact pressures between the diaper and the baby were also calculated as the diaper was applied. FIGS. 18 and 19 show the contact pressures at different moments during the application. The diaper is hidden in these pictures so that the effects of the diaper on the baby can be easily visualized. It was necessary to reduce the element size on the user for this simulation so that accurate readings of contact pressure could be obtained. Contact pressure could be used to investigate diaper gaps (potential leakage sites), which have no contact pressure, and potential redmarking sites, which are areas of higher contact pressure. Diaper designs can then be modified based on the results of such simulations to obtain consistent pressures around the whole gasket that are not so high as too cause redmarking but high enough to prevent gapping.

Simulations were run with varying diaper coefficients of friction between the diaper and the torso from 0 to 3. Between 0 and 0.5 no significant difference was found in the deformation or contact pressure results. At a friction coefficient of 3, the contact pressure was only slightly different, but the positioning of the diaper did vary. It was found that at higher levels of friction the diaper sits lower at the waist and on the leg. Additionally, as the friction level is increased, the results become more sensitive to the method of diaper application.

Embodiment 1c

The third embodiment included a dynamic wearer with an internal bone structure, joints, and deformable soft tissue. In this embodiment, deformation of the product and wearer were investigated along with stresses, contact pressures, and force vectors over a range of wearer motion. To incorporate motion into the user, it was necessary to update the user from a rigid model with a compliant surface to a completely soft model with an internal bone structure. The model was given a simplified backbone, pelvis, and two femurs. Specifications of the material properties for both the soft tissue and the bones in this embodiment are summarized Table 3below.

It should be noted that these values may be altered based upon the desired characteristics of the wearer to be modeled.

TABLE 3

Material definitions and material property data for the virtual wearer.

| | Element type | Density (tonne/mm$^3$) | Young's modulus (MPa) | Poisson's Ratio |
|---|---|---|---|---|
| Bone | B31 | $7.8*10^{-6}$ | $2.07*10^8$ | 0.292 |
| Soft Tissue | C3D4 | $1*10^{-9}$ | 0.5 | 0.3 |

Figure 20:
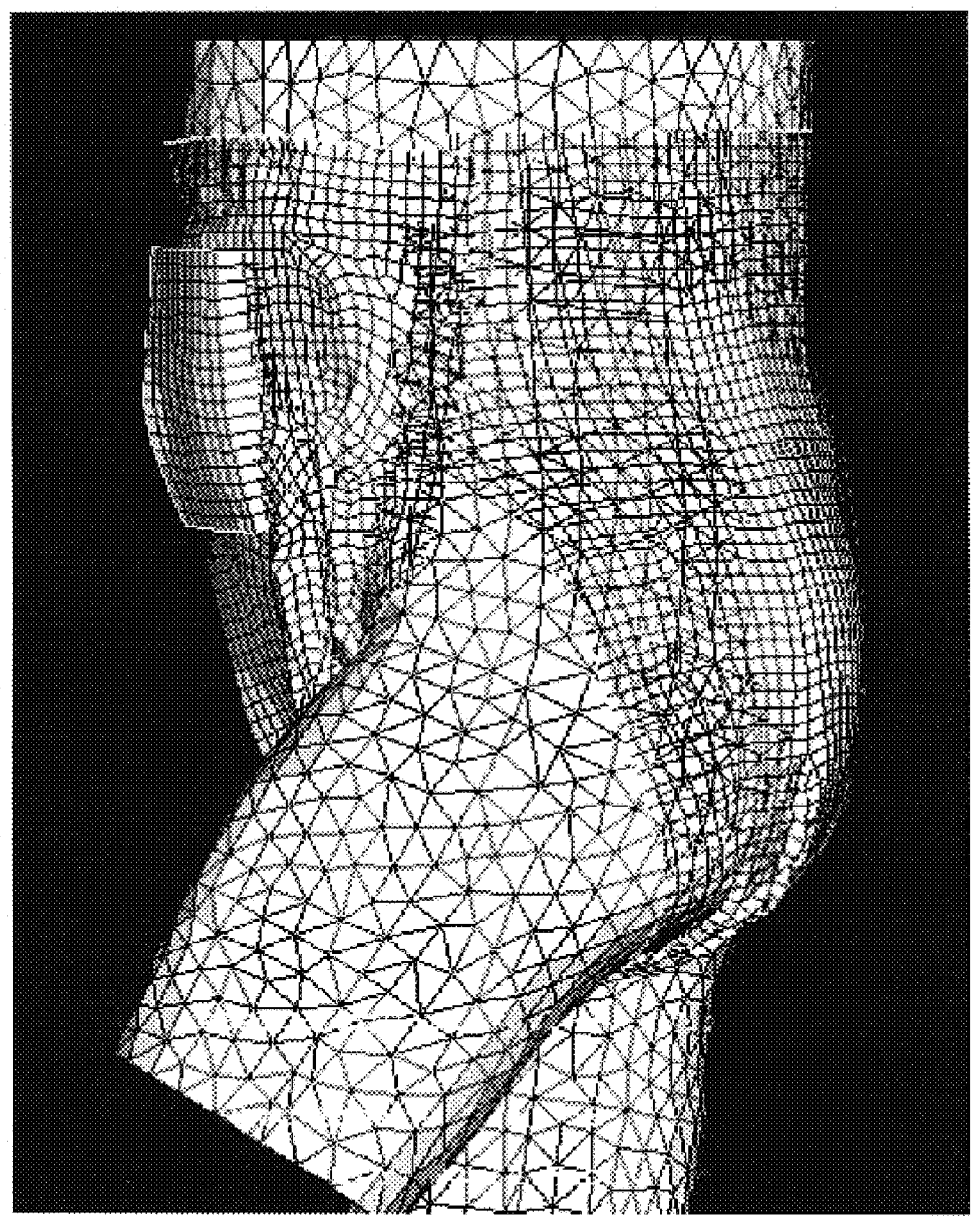
FIG. 20 is a perspective representation of the wearer walking with the product.

The elements chosen to represent the bones were beam elements. This type of element was chosen because it is good for components in which the length dimension is significantly greater than the other two dimensions (such as the femurs and backbone). The soft tissue was modeled with continuum elements that are flexible enough to adequately represent almost any shape and loading. These elements model small blocks of material in a component and can be connected to each other on any face. This allows for the versatility to model the complex shape of the infant torso. Once the torso was updated with a bone structure to allow for movement, motion could be applied to the model. The average hip motion of 2 year olds during walking was obtained for use in the simulation. (See Sutherland et al., *The Development of Mature Walking*, MacKeith Press, London, England, 1998, illustrating graphs that depict the hip angle versus percent gait cycle.) A representative depiction of the virtual user walking may be found in FIG. 20.

Figure 21:
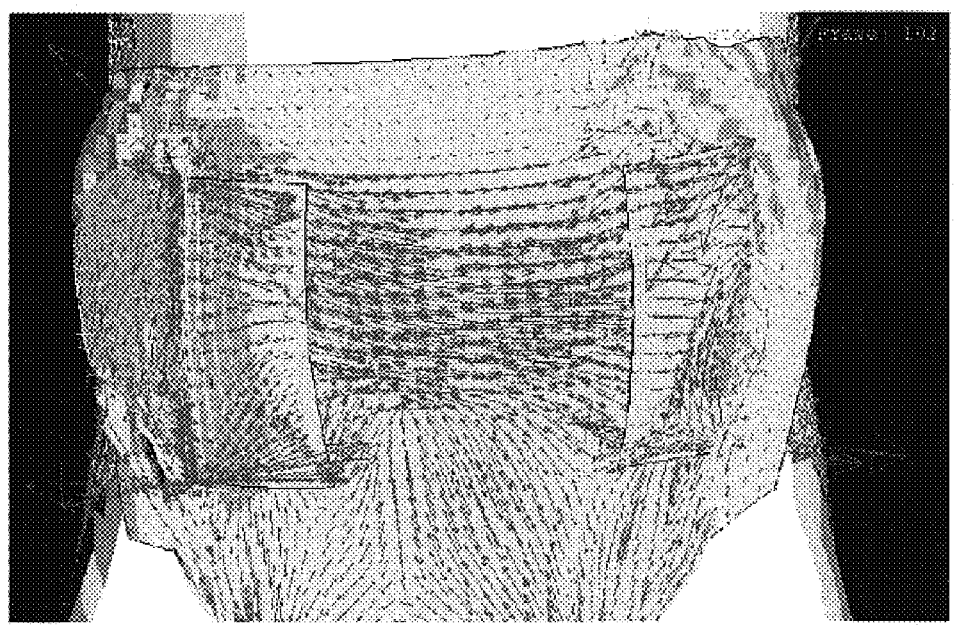
FIG. 21 is a perspective representation of forces on the product represented as vectors.

The simulation output included diaper and wearer deformation, product stresses, and contact pressures between the product and wearer through the entire process of applying the diaper and moving the wearer through the walking motion. The force vectors for every element of the diaper were also output throughout the simulation. This type of output aids in the analysis of different product designs. Specifically, it can be used to analyze force magnitudes and directions, noting any large vectors such as those highlighted in FIG. 21. Different diaper designs may be compared to display force variations. Reduction of large forces may lead to better fit maintenance or a reduction of diaper failures (i.e., ear tears).

Example 2—Feminine Care Pad

Additional features of the feminine care pad embodiment are discussed below. Appendix 2 provides an example of the input files for the feminine care pad embodiments. In one embodiment, a typical feminine pad wearer was determined from available usage, demographic, and/or anthropometric data and modeled as the representative wearer. A representative wearer for the feminine pad is defined as a person that is 5 feet 6 inches tall, weighs 140 pounds, and has waist, hip, and thigh measurements of 27 inches, 41 inches, and 24 inches, respectively. To specify the geometry of the wearer, a point cloud of an adult female with similar body measurements to those listed above was identified from the CAE-SAR database. The point cloud was then converted into a Finite Element mesh using software programs such as Geomagic, Ideas or Abaqus/CAE. Material property definitions used to describe wearer soft tissue behavior have used a Neo-Hookean hyperelastic material model. Bones can be treated as rigid or as elastic. Skin can be defined as either a layer of shell or membrane elements over the soft tissue volume and is typically given the same material behavior as the underlying soft tissue.

To improve the virtual wearer sub-model 20, quasi-spherical volumes of simulated material are removed from the finite element model in the regions surrounding the hip joints 60 of FIG. 5. This is done to allow for a greater range of motion of the leg which would be inhibited due to deformation and possible failure (due to excessive deformation) of the elements in the regions surrounding the hip joints 60 because of modeling simplifications of the soft tissue and joints. Similar failure in the physical foam torso material in these regions was noted resulting in tears that could propagate to the model surface.

The product sub-model 22 is simplified to reduce calculational complexity only modeling the two solid layers 83, 85 as illustrated in FIG. 9. Alternately, in one embodiment, a continuous mesh between the distribution and shaping layers 83, 85 is used instead of contact modeling. Slots in the distribution layer are modeled and retained, as these slots tend to focus the deformation during movement, such as when the wearer closes her legs. The simplified product consists of the two thick layers, the distribution layer 83, and the shaping layer 85, bonded at their interface. This simplification reduces numerical problems encountered with the stacked design, but allows for the general product deformations observed in visualization of the product in conjunction with the foam torso test stand.

Figure 22:
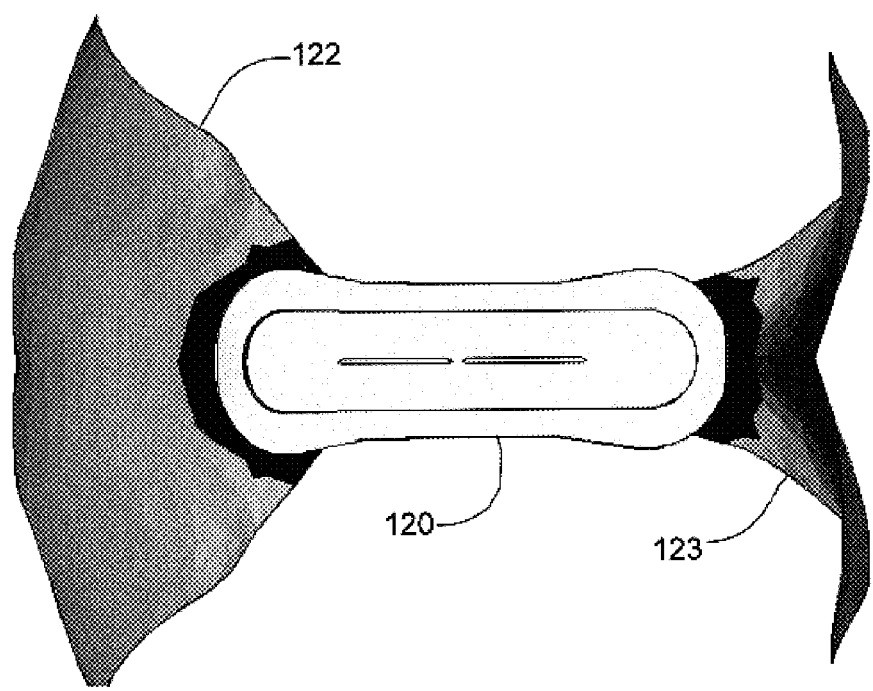
FIG. 22 is a schematic plan representation of a panty and a rigid surface used to apply the product of FIG. 9.

An environmental sub-model was also created to represent a panty, generally indicated at 120. A depiction of the product sub-model 22 and panty sub-model is illustrated in FIG. 22. The virtual panty model 120 is used on the simplified torso application runs. The panty as modeled is initially flat and without material away from V-shaped regions 122, 123 at the front and rear. Panty waistbands (not shown) are pulled up and toward the torso by enforced displacements. Lines of beams are desirable along each waistband to provide lateral stiffness to avoid numerical problems with modeling as will be understood by one skilled in the art. Table 4 lists the material definitions and material property data of the feminine care pad, the panty and the representative wearer.

Application of the product involves the virtual panty model 120 being moved down and the waistbands moved away from the torso, from the original, neutral position to a position that permits the virtual product sub-model 22 to be captured between the virtual panty model 120 and the virtual wearer sub-model 20. The motion of the waistbands can then be reversed, allowing the virtual panty model 120 to return to the known waistband locations, thus applying the virtual product sub-model 22 to the torso with reasonable restraint forces. It was found that the virtual wearer sub-model 20 had many small element faces in the torso 52 to leg 54 transitional areas that presented some issues in the numerical stability of the panty component. The panty was remeshed in this region, keeping the same outline and topology, but replacing many of the smaller elements with several larger elements closer to the average element size in the rest of the panty. Panty models of various types of panties (e.g., bikini, briefs, etc.) can be generated and tested with the use model 30.

The use model 30 is used to determine if the virtual product sub-model 22 can be applied to the torso with the virtual panty 120, or if the panty can only be used to contain the product after application. An explicit integration based finite element software should be used for the application process because of the many contact interactions that are active. To achieve reasonable run times, the technique of mass scaling can be used to increase the stable time increment. It was seen that appropriate mass scaling allows the simulation to proceed using larger stable time increments without adversely affecting the validity of the simulation result. This causes the panty to deform and stretch without moving the product against the torso.

In one embodiment, a rigid surface or pad pusher (not shown) was modeled to push the product 80 against the torso 52 and then move away, allowing the panty model 120 to retain the product 80 against the torso. This rigid surface is based upon the topology of the panty that would come into contact with the product during installation. The initial position of the surface is slightly above the panty surface,

TABLE 4

Material definitions and material property data for the virtual wearer and virtual feminine care pad.

| Component | Element Type | Thickness (mm) | Density (tonne/mm3) | Material Model | Young's Modulus (MPa) | Poisson's Ratio | Other Parameters |
|---|---|---|---|---|---|---|---|
| foam (body) | C3D4 | n/a | $1.00*10^{-9}$ | Hyperelastic | n/a | n/a | c10 = 1.0 (MPa), c01 = 0.0 (MPa), D = 0.05 ($MPa^{-1}$) |
| skin | M3D3 | 1.00E-04 | $1.00*10^{-9}$ | Hyperelastic | n/a | n/a | c10 = 1.0 (MPa), c01 = 0.0 (MPa), D = 0.05 ($MPa^{-1}$) |
| distribution | C3D8R | n/a | $1.40*10^{-10}$ | Elastic/Plastic | 16.8 | 0.1 | plastic (MPa, mm/mm) {{0.24, 0.0}, {0.31, 0.0073}, {0.62, 0.014}} |
| lycra | T3D2 | 1 | $1.00*10^{-10}$ | Elastic | 100 | 0.3 | |
| shaping | C3D8R | n/a | $8.00*10^{-11}$ | Elastic/Plastic | 2.79 | 0.1 | plastic (MPa, mm/mm) {{0.051, 0.0}, {0.97, 0.0036}, {0.17, 0.015}} |
| panty | M3D3 | 0.1 | $1.00*10^{-10}$ | Hyperelastic | n/a | n/a | c10 = 1.0 (MPa), c01 = 0.0 (MPa), D = 0.05 ($MPa^{-1}$) | and its motion history is slightly in advance of the panty motion. This avoids any problems with duplicate contact conditions on the product from the panty during installation. The surface is quickly moved away from the product once the application is complete to allow the panty to take over the contact interaction that would retain the product against the torso.

To obtain suitable virtual product response, it is desirable that the restraint conditions imposed by the panty are as close to reality as possible. In one detailed model, the virtual panty model 120 is still only composed of the V-shaped regions 122,123 at the front and rear of the panty, but the initial shape is not arbitrary and flat, but rather based upon the topology of the standing torso. A coating of membrane elements is placed upon the standing torso, and then modified to obtain a straight panty waistband at the front and rear. The edges of the panty mesh connecting the front and rear waistbands on either side of the panty are also modified to yield as smooth a transition as possible. The virtual panty in the detailed model is related to the torso in overall topology, and the location of the waistbands in a neutral applied position is known.

Figure 23:
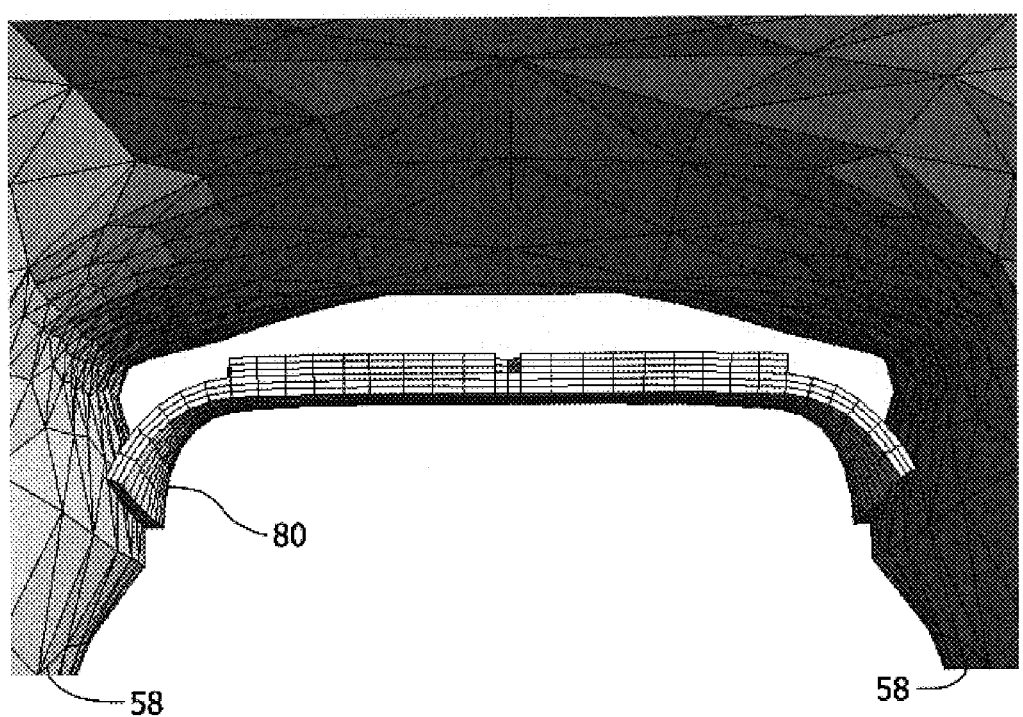
FIG. 23 is a schematic cross-sectional representation of the representative product of FIG. 22 in conjunction with a representative wearer.
Figure 24:
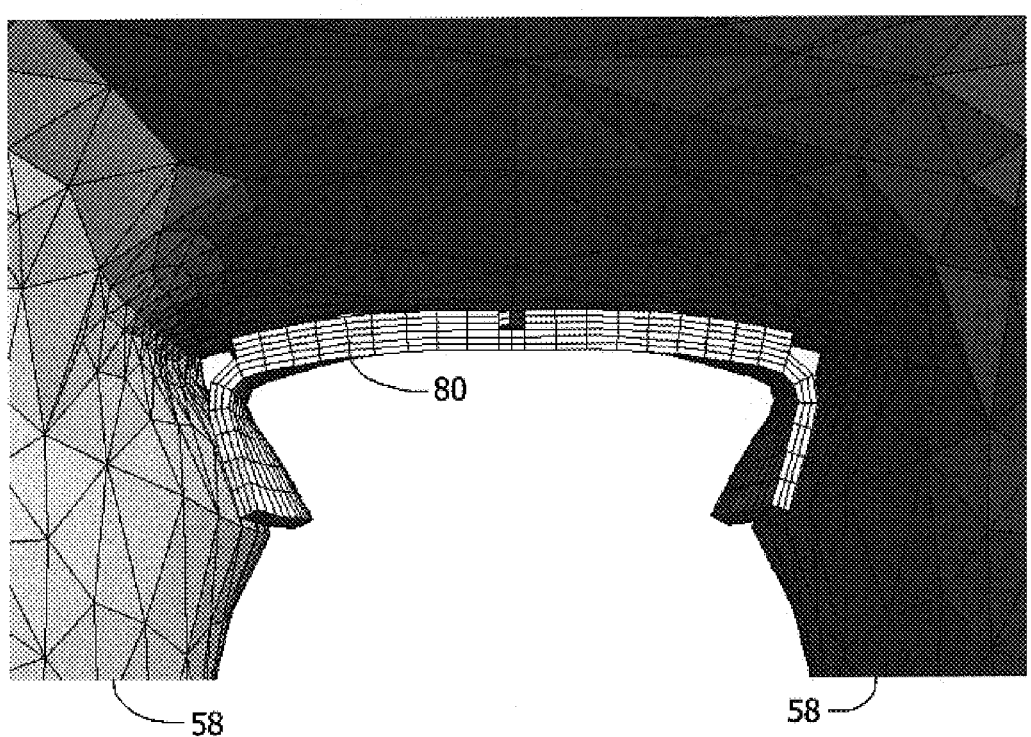
FIG. 24 is a schematic cross-sectional representation of the wearer with the representative product in place.
Figure 25:
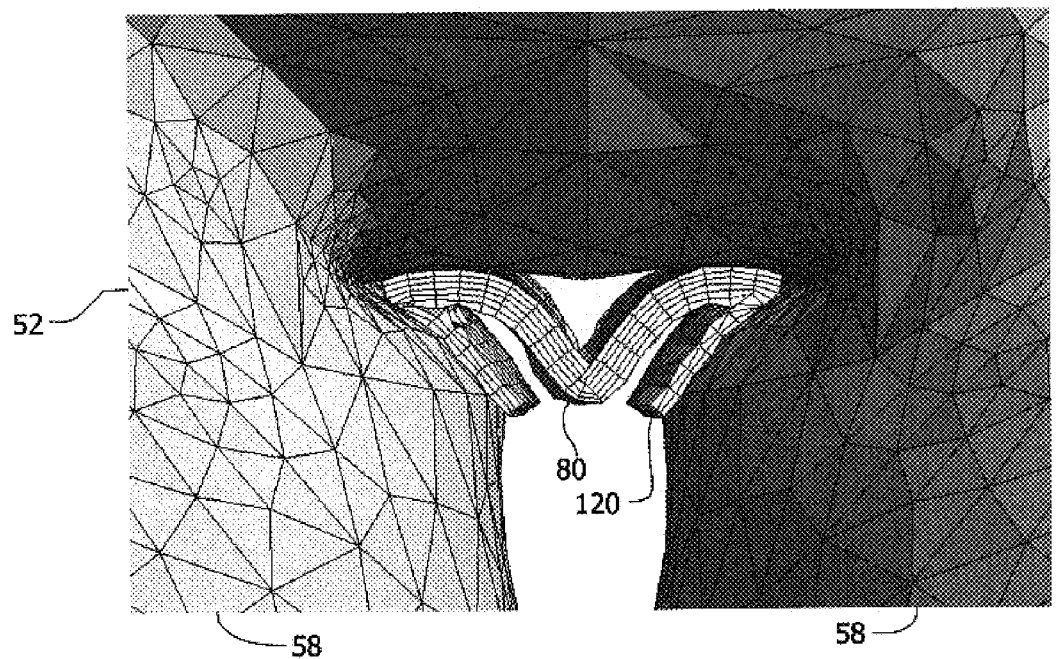
FIG. 25 is a schematic cross-sectional representation of the wearer after thighs have moved together illustrating deformation of the product.

FIGS. 23–25 are cross-sectional views of one embodiment of the product 80, illustrated as a feminine care pad, showing the product/torso deformations during product installation onto the torso 58 followed by leg closure. In the example shown, the product 80 is initially deformed onto a standing torso 58 with legs spread at an 18 degree angle using the rigid surface (not shown) and the conformal panty (not shown). This allows the product 80 to conform to the torso 58 over the entire area of the product. Because the legs have to be spread during the initial product application, the panty only consists of the V-shaped regions (122, 123 of FIG. 22) at the front and rear of the torso. Using the V-shaped region simplifies the application process because a full panty would not have to be pulled up and over the outer thighs with the legs spread. Once the product 80 is snug against the torso 58 as illustrated in FIG. 24, the rigid surface is removed, and the panty is allowed to provide the retention force by controlling the waistband position against the torso.

With the product, panty, and torso in their as-installed positions, the legs are closed as illustrated in FIG. 25. In one embodiment, closing the legs results in the outer edges of the shaping layer 85 near the center of the product 80 being bent down by contact with the thighs, while the rest of the product, mainly the distribution layer 83, is in partial contact with the torso 58. When the legs are closed, the deformation pattern of the product 80 closely resembles the deformation seen in test stand data.

Use of a conformal panty model 120 and known waistband locations ensure that the retention forces after product installation are reasonable. Because the panty model 120 provides the base for the product 80 in actual use, the interaction of the panty with not only the product, but also with the articulating torso 58, should be well defined.

The method and apparatus described herein has the advantage of being able to model a product being put on as a wearer would put it on, in addition to modeling the product while the product is being worn. Also, the method and apparatus described herein provide dynamic modeling of the product in use, as opposed to previous systems that typically provide only static modeling. In addition, the computer-based modeling of virtual products and uses can examine features and results that cannot be seen through physical testing. Finally, the apparatus and method can be used for optimization modeling; a product developer selects a desired product performance, and the model designs a product that will meet that performance.

The invention described herein provides an improved method to virtually evaluate and design products. Virtual development does not have the limitations of resource and material availability, or safety issues associated with human testing. Virtual development allows exploration of concepts not achievable previously using conventional methods. This virtual advantage expedites innovations by allowing new products to get to market faster and with less cost.

While the invention has been described in conjunction with several specific embodiments, it is to be understood that many alternatives, modifications and variations will be apparent to those skilled in the art in light of the foregoing description. Accordingly, this invention is intended to embrace all such alternatives, modifications and variations that fall within the spirit and scope of the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A method of designing a product to be worn on a body, the method comprising:

creating a computer based body sub-model of at least a portion of the body on which the product is to be positioned;

creating a computer based product sub-model of the product;

defining an environment in which the body sub-model interacts with the product sub-model with an environment sub-model;

interacting the body sub-model, the product sub-model, and the environment sub-model with movement of one or more of the sub-models with an interaction model;

combining the body sub-model, the product sub-model, the environment sub-model and the interaction model in a use model simulating the interaction between the body sub-model, the product sub-model and the environment sub-model to produce a representation of at least one product feature of the product; and evaluating the use model to determine the performance of the at least one product feature of the product; and modifying the product sub-model in response to the performance of said product feature and reperforming the steps of interacting and combining the models in the use model and evaluating the use model to determine performance of the at least one product feature.

2. A method of designing a product for use on a body according to claim 1 further comprising reperforming the step of modifying the product sub-model until desired performance of said at least one performance feature is obtained to design the product.

3. A method of designing a product for use on a body according to claim 1 wherein the use model determines the forces, stresses and/or strains in the body sub-model and the product sub-model when the interaction model simulates movement of the body.

4. A method of designing a product for use on a body according to claim 1 wherein the environment sub-model comprises environmental elements that interact with the product sub-model and the body sub-model.

5. A method of designing a product for use on a body according to claim 4 wherein the environmental elements are selected from the group consisting of garments, a car seat, a table and a bed.

6. A method of designing a product for use on a body according to claim 5 wherein the environmental elements comprise a computer based model of a garment worn with the product.

7. A method of designing a product for use on a body according to claim 1 wherein the use model determines the interaction between the body sub-model, the product sub-model and/or the environment sub-model during simulated movement of the body.

8. A method of designing a product for use on a body according to claim 7 wherein evaluating the use model further comprises determining the performance of at least one product feature of the environmental elements.

9. A method of designing a product for use on a body according to claim 7 wherein the use model determines the interaction between the sub-models using numerical method analysis.

10. A method of designing a product for use on a body according to claim 9 wherein the use model performs a finite element analysis using the body sub-model, the product sub-model and the environment sub-model.

11. A method of designing a product for use on a body according to claim 1 wherein the body sub-model comprises at least one of a geometry sub-model, a material properties sub-model, an initial conditions sub-model, kinematic constraints of the body sub-model and/or contact constraints of the body sub-model.

12. A method of designing a product for use on a body according to claim 11 wherein the geometry sub-model comprises coordinates defining an exterior surface of the body.

13. A method of designing a product for use on a body according to claim 11 wherein the geometry sub-model comprises coordinates defining the relationship between internal components of the body to the exterior surface.

14. A method of designing a product for use on a body according to claim 11 wherein the material sub-model defines material property characteristics of the body.

15. A method of designing a product for use on a body according to claim 11 wherein the contact constraints dictate interaction between components of the body sub-model.

16. A method of designing a product for use on a body according to claim 11 wherein the kinematic constraints restrict motions of the body sub-model.

17. A method of designing a product for use on a body according to claim 1, wherein the body sub-model is selected to be representative of a consumer of the product.

18. A method of designing a product for use on a body according to claim 1, wherein the act of creating a body sub-model comprises modeling the internal structure of the body.

19. A method of designing a product for use on a body according to claim 1, wherein the computer based body sub-model is one of a plurality of body sub-models on which the product is positioned.

20. A method of designing a product for use on a body according to claim 1 wherein the product sub-model comprises at least one of a geometry sub-model, a material properties sub-model, an initial conditions sub-model, kinematic constraints of the product sub-model and/or contact constraints of the product sub-model.

21. A method of designing a product for use on a body according to claim 20 wherein the geometry sub-model comprises coordinates defining an exterior surface of the product.

22. A method of designing a product for use on a body according to claim 20 wherein the material sub-model defines material property characteristics of the product.

23. A method of designing a product for use on a body according to claim 22 wherein the material property characteristics of the product are selected based on conditions of the product during use.

24. A method of designing a product for use on a body according to claim 23 wherein the conditions used to select material property characteristics comprise at least one of temperature, humidity and/or deformation.

25. A method of designing a product for use on a body according to claim 20 wherein the contact constraints dictate interaction between components of the product sub-model.

26. A method of designing a product for use on a body according to claim 20 wherein the kinematic constraints restrict motions of the product sub-model.

27. A method of designing a product for use on a body according to claim 1, wherein the product sub-model is one of a plurality of product sub-models of the product, wherein each product sub-model defines a different product geometry and/or material property of the product.

28. A method of designing a product for use on a body according to claim 1 wherein the interaction model comprises field variables, kinematic instructions, loading instructions, and contact constraint instructions.

29. A method of designing a product for use on a body according to claim 1 wherein the product feature evaluated is selected from the group consisting of product deformation, product stresses, product force vectors, product curvature, contact pressure, surface area of coverage, and conformance to the body surface area.

30. A method of designing a product for use on a body according to claim 1 wherein the product feature evaluated is selected from the group consisting of the contact pressure on the body, the integral of the pressure over the contact area, the appearance of the product when worn by the body, deformation of the body caused by the product, and the contact area between the body and the product.

31. A method of designing a product for use on a body according to claim 1 wherein the performance of a product feature determined by evaluating the use model is selected from the group consisting appearance of a garment worn with the product, the contact area between the garment and the product, and the appearance of the product when in contact with an external article.

32. A method of designing a product for use on a body according to claim 1, wherein the use model calculates forces applied by the body sub-model on the product sub-model during the simulated interaction.

33. A method of designing a product for use on a body according to claim 1, wherein the act of creating the use model comprises modeling an elapse of time during which the movement of the body sub-model interacts with the product sub-model.

34. A method of designing a product for use on a body according to claim 1, wherein the product is an article of clothing.

35. A method of designing a product for use on a body according to claim 1, wherein the product is an absorbent product.

36. A method of designing a product for use on a body according to claim 1, wherein the product is a diaper.

37. A method of designing a product for use on a body according to claim 1, wherein the product is a feminine care pad.

* * * * *